US012788222B2

(12) United States Patent
Zhao et al.

(10) Patent No.: US 12,788,222 B2
(45) Date of Patent: Nov. 10, 2026

(54) DEVICES AND SYSTEMS FOR BODY CAVITIES AND METHODS OF USE

(71) Applicant: Drive Medical, Inc., Claremont, CA (US)

(72) Inventors: Yan Shi Zhao, Claremont, CA (US); Corbett W. Stone, Buckeye, AZ (US); Christopher W. Maurer, Wakefield, MA (US)

(73) Assignee: Drive Medical, Inc., Claremont, CA (US)

( * ) Notice: Subject to any disclaimer, the term of this patent is extended or adjusted under 35 U.S.C. 154(b) by 633 days.

(21) Appl. No.: 17/271,552

(22) PCT Filed: Aug. 27, 2019

(86) PCT No.: PCT/US2019/048393

§ 371 (c)(1),
(2) Date: Feb. 25, 2021

(87) PCT Pub. No.: WO2020/046979

PCT Pub. Date: Mar. 5, 2020

(65) Prior Publication Data

US 2021/0345862 A1 Nov. 11, 2021

Related U.S. Application Data

(60) Provisional application No. 62/723,449, filed on Aug. 27, 2018.

(51) Int. Cl.

| | |
|---|---|
| ***A61B 1/00*** | (2006.01) |
| ***A61B 1/005*** | (2006.01) |

(Continued)

(52) U.S. Cl.

CPC ...... *A61B 1/00156* (2013.01); *A61B 1/00082* (2013.01); *A61B 1/00096* (2013.01);

(Continued)

(58) Field of Classification Search

CPC ............ A61B 1/00156; A61B 1/00082; A61B 1/00096; A61B 1/00154; A61B 1/0058;

(Continued)

(56) References Cited

U.S. PATENT DOCUMENTS

| | | | |
|---|---|---|---|
| 4,148,307 | A | 4/1979 | Utsugi |
| 4,176,662 | A | 12/1979 | Frazer |

(Continued)

FOREIGN PATENT DOCUMENTS

| | | | |
|---|---|---|---|
| CN | 105025973 | A | 11/2015 |
| EP | 2614765 | A1 | 7/2013 |

(Continued)

OTHER PUBLICATIONS

Gao et al., "Locomotion system of pneumatic inchworm-like microrobot for intestinal tract," Beijing Biomed Eng. (2012) 31(5): 487 Article in Chinese Language; English abstract provided.

*Primary Examiner* — Anhtuan T Nguyen
*Assistant Examiner* — James Edward Boice
(74) *Attorney, Agent, or Firm* — Morrison & Foerster LLP

(57) ABSTRACT

The present disclosure relates to a device configured to move within a body cavity, such as the gastrointestinal tract, in particular, the small intestine, and methods of using the device. The presently disclosed device may be self-driving, and the articulation of a tip of the device may be controlled and fine tuned. The presently disclosed device may be used in a variety of body cavities such as a vascular body lumen, a digestive body lumen, a respiratory body lumen, or a urinary body lumen, for example, for endoscopic purposes, for delivering a substance into the body cavity, for removing a substance or tissue from the body cavity, for capturing an image of the body cavity, and/or for performing an operation of a tissue or organ using the device.

23 Claims, 23 Drawing Sheets

(51) Int. Cl.

| | |
|---|---|
| ***A61B 1/01*** | (2006.01) |
| ***A61B 1/015*** | (2006.01) |
| *A61B 1/273* | (2006.01) |
| *A61B 1/31* | (2006.01) |
| *A61M 25/10* | (2013.01) |

(52) U.S. Cl.
CPC ........ *A61B 1/00154* (2013.01); *A61B 1/0058* (2013.01); *A61B 1/01* (2013.01); *A61B 1/015* (2013.01); *A61B 1/2733* (2013.01); *A61B 1/2736* (2013.01); *A61B 1/31* (2013.01); *A61M 2025/1004* (2013.01); *A61M 2025/1015* (2013.01); *A61M 25/1018* (2013.01)

(58) Field of Classification Search
CPC ......... A61B 1/01; A61B 1/015; A61B 1/2733; A61B 1/2736; A61B 1/31; A61B 2017/22054; A61B 2017/3486; A61B 1/0008; A61B 2017/003; A61B 2017/00318; A61B 2034/301; A61B 1/0057; A61B 1/0011; A61M 25/1018; A61M 25/1006; A61M 25/1004; A61M 25/1015
USPC .......................... 600/115; 604/95.03, 101.05
See application file for complete search history.

(56) References Cited

U.S. PATENT DOCUMENTS

| | | | | |
|---|---|---|---|---|
| 4,911,163 | A | 3/1990 | Fina | |
| 5,337,732 | A | 8/1994 | Grundfest et al. | |
| 5,662,587 | A * | 9/1997 | Grundfest | A61B 1/0051 600/116 |
| 6,007,482 | A | 12/1999 | Madni et al. | |
| 6,409,658 | B1 * | 6/2002 | Mitsumori | A61B 1/00188 600/130 |
| 6,899,672 | B2 | 5/2005 | Chin et al. | |
| 7,503,904 | B2 | 3/2009 | Choi | |
| 7,708,687 | B2 | 5/2010 | Bern et al. | |
| 7,798,992 | B2 | 9/2010 | Ortiz | |
| 7,879,004 | B2 | 2/2011 | Seibel et al. | |
| 7,892,469 | B2 | 2/2011 | Lim et al. | |
| 8,303,484 | B2 | 11/2012 | Hopper et al. | |
| 8,469,926 | B2 | 6/2013 | Pepper et al. | |
| 9,061,118 | B2 | 6/2015 | Shoham et al. | |
| 11,944,262 | B2 | 4/2024 | Toshio et al. | |
| 2003/0065250 | A1 * | 4/2003 | Chiel | A61B 34/72 600/115 |
| 2005/0272976 | A1 | 12/2005 | Tanaka et al. | |
| 2006/0257234 | A1 | 11/2006 | Park | |
| 2007/0106302 | A1 | 5/2007 | Ortiz | |
| 2008/0091073 | A1 | 4/2008 | Park | |
| 2008/0103440 | A1 | 5/2008 | Ferren et al. | |
| 2009/0069821 | A1 * | 3/2009 | Farritor | A61B 5/073 606/130 |
| 2009/0149711 | A1 * | 6/2009 | Tanaka | A61B 1/0052 600/152 |
| 2009/0171369 | A1 * | 7/2009 | Gayzik | A61M 25/1011 606/127 |
| 2009/0234279 | A1 | 9/2009 | Goldstein | |
| 2009/0326490 | A1 * | 12/2009 | McMichael | A61F 5/451 604/328 |
| 2010/0022947 | A1 | 1/2010 | Hassidov et al. | |
| 2010/0041951 | A1 | 2/2010 | Glozman et al. | |
| 2010/0222811 | A1 | 9/2010 | Gellman | |
| 2011/0060186 | A1 | 3/2011 | Tilson | |
| 2013/0178828 | A1 * | 7/2013 | Takagi | A61M 25/0084 604/506 |
| 2013/0267775 | A1 * | 10/2013 | Okamoto | A61B 1/0016 600/109 |
| 2014/0066939 | A1 | 3/2014 | Kaiser et al. | |
| 2014/0214070 | A1 * | 7/2014 | Vardi | A61B 17/221 606/200 |
| 2014/0243855 | A1 * | 8/2014 | Sholev | A61B 17/068 606/139 |
| 2016/0059292 | A1 * | 3/2016 | Sato | H02K 7/14 72/448 |
| 2016/0114141 | A1 | 4/2016 | Mabry et al. | |
| 2017/0086653 | A1 | 3/2017 | Yeung et al. | |
| 2017/0203080 | A1 | 7/2017 | Terliuc et al. | |
| 2019/0388133 | A1 * | 12/2019 | Sharma | A61B 18/04 |
| 2023/0079408 | A1 | 3/2023 | Zhao et al. | |
| 2024/0041301 | A1 | 2/2024 | Zhao | |

FOREIGN PATENT DOCUMENTS

| | | | |
|---|---|---|---|
| EP | 2278908 | B1 | 6/2021 |
| JP | 2012075595 | A | 4/2012 |
| JP | 2015042321 | A | 3/2015 |
| WO | WO2005074377 | A2 | 8/2005 |
| WO | 2015/123313 | A1 | 8/2015 |
| WO | WO 2020/046979 | | 3/2020 |
| WO | WO2020194568 | A1 | 10/2020 |
| WO | WO 2021/173818 | | 9/2021 |
| WO | 2022140468 | A1 | 6/2022 |

* cited by examiner

DEVICES AND SYSTEMS FOR BODY CAVITIES AND METHODS OF USE

CROSS-REFERENCE TO RELATED APPLICATIONS

This application is a national stage application under 35 U.S.C. § 371 of International Application No. PCT/US2019/048393 filed Aug. 27, 2019, which claims priority from U.S. provisional application No. 62/723,449 filed Aug. 27, 2018, entitled "Gastrointestinal Navigation and Delivery Device," which application are incorporated herein by reference in their entirety.

FIELD

The present disclosure relates to a device configured to move within a body cavity, such as the gastrointestinal tract, in particular, the small intestine, and methods of using the device for endoscopic purposes, for delivering a substance into the body cavity, for removing a substance or tissue from the body cavity, for capturing an image of the body cavity, and/or for performing an operation of a tissue or organ using the device. The presently disclosed device may be self-driving, and the articulation of a tip of the device may be controlled and fine tuned. The presently disclosed device may be used in a variety of body cavities such as a vascular body lumen, a digestive body lumen, a respiratory body lumen, or a urinary body lumen.

BACKGROUND

The current endoscopic procedures, such as esophagogastroduodenoscopy (EGD), colonoscopy, enteroscopy, etc., involve intensive human operation of the systems. For instance, it is generally known that a gastrointestinal examination uses an endoscope having a flexible insertion section. In inserting the above-mentioned endoscope into deep part of the digestive tract, e.g., the small intestine, when the insertion section is inserted thereinto while being pushed, a force is hardly transmitted to the distal end of the insertion section because the intestine is complicatedly curved. It is, therefore, difficult to insert the insertion section into deep part. Oftentimes, even when it is possible to insert an endoscope into deep part, it takes a long time, causes discomfort and pain, and requires sedation. Thus, there is need for a device that is easy to use and causes less discomfort. The present disclosure addresses these and other needs.

SUMMARY

In some aspects, provided herein is a device configured to move within a body cavity, said device comprising: an outer member comprising a distal end, a proximal end, and a lumen between the distal end and the proximal end; an inner member slidably disposed in the lumen of the outer member, wherein the inner member comprises a distal end and a proximal end; a first controllably expandable element; a second controllably expandable element; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

In some aspects, provided herein is a device configured to move within a body cavity, said device comprising: an outer member comprising a distal end, a proximal end, and a lumen between the distal end and the proximal end; an inner member slidably disposed in the lumen of the outer member, wherein the inner member comprises a distal end and a proximal end; a first controllably expandable element disposed on the outer member or on the inner member; a second controllably expandable element disposed on the outer member or on the inner member; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

In some aspects, provided herein is a device configured to move within a body cavity, said device comprising: an outer member comprising a distal end, a proximal end, and a lumen between the distal end and the proximal end; an inner member slidably disposed in the lumen of the outer member, wherein the inner member comprises a distal end and a proximal end; a first controllably expandable element disposed on the outer member; a second controllably expandable element disposed on the outer member or on the inner member; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

In some aspects, provided herein is a device configured to move within a body cavity, said device comprising: an outer member comprising a distal end, a proximal end, a lumen between the distal end and the proximal end, and a first controllably expandable element; an inner member slidably disposed in the lumen of the outer member, wherein the inner member comprises a distal end, a proximal end, and a second controllably expandable element; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

In some aspects, provided herein is a device configured to move within a body cavity, said device comprising: an outer member comprising a distal end, a proximal end, a lumen between the distal end and the proximal end, a first controllably expandable element, and a second controllably expandable element; an inner member slidably disposed in the lumen of the outer member, wherein the inner member comprises a distal end and a proximal end; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

In any of the preceding embodiments, the inner member can comprise one or more aperture on the distal end. In any of the preceding embodiments, the inner member can comprise one or more channel.

In any of the preceding embodiments, the device can further comprise an articulation element capable of effecting articulation of the distal end of the inner member or the distal end of the outer member. In some aspects, the articulation element is capable of effecting articulation of the distal end of the inner member.

In any of the preceding embodiments, the first controllably expandable element can be disposed on an outer surface of the outer member. In any of the preceding embodiments, the second controllably expandable element can be disposed on an outer surface of the inner member. In any of the preceding embodiments, the first and second controllably expandable elements may be both disposed on the outer member. In any of the preceding embodiments, the first and second controllably expandable elements may be both disposed on the inner member.

In any of the preceding embodiments, the inner member can extend through the first lumen of the outer member, and/or the second controllably expandable element can be outside the first lumen of the outer member.

In any of the preceding embodiments, the first controllably expandable element can comprise or be a first balloon, and/or the second controllably expandable element can comprise or be a second balloon.

In any of the preceding embodiments, the device can further comprise a first medium channel connected to the first controllably expandable element, wherein the medium comprises a gas, a liquid, or a mixture thereof (e.g., a vapor). In some aspects, the first medium channel is inside the outer member. In some aspects, the first medium channel is outside the outer member. In some aspects, the first medium channel is partially inside and partially outside the outer member.

In any of the preceding embodiments, the device can further comprise a second medium channel connected to the second controllably expandable element, wherein the medium comprises a gas, a liquid, or a mixture thereof (e.g., a vapor). In some aspects, the second medium channel is inside the inner member. In some aspects, the second medium channel is outside the inner member. In some aspects, the second medium channel is partially inside and partially outside the inner member. In any of the preceding embodiments, the first and second medium channels can be separate channels.

In any of the preceding embodiments, the device can further comprise a control member. In some aspects, the control member is configured to independently expand and/or contract the first and second controllably expandable elements. In any of the preceding embodiments, the control member may be configured to control the actuating member, thereby controlling the sliding movement between the outer member and the inner member.

In any of the preceding embodiments, the inner member can comprise a body portion and a distal portion comprising the distal end of the inner member. In some aspects, the second controllably expandable element is disposed on the distal portion of the inner member. In any of the preceding embodiments, the distal end of the inner member can comprise two or more apertures. In some aspects, at least one of the apertures is for an image capturing device. In any of the preceding embodiments, at least one of the apertures can be for a gas, liquid, or suction channel.

In any of the preceding embodiments, the proximal end of the distal portion can comprise one or more controllably expandable base.

In any of the preceding embodiments, the device can further comprise an articulation element capable of effecting articulation of the distal end of the inner member. In some aspects, the articulation element comprises a motor. In any of the preceding embodiments, the articulation element can comprise one or more controllably expandable base on the proximal end of the distal portion. In some aspects, the one or more controllably expandable base is configured to inflate and/or deflate, thereby effecting articulation of the distal portion in a direction transverse to the longitudinal axis of the body portion. In any of the preceding embodiments, the device can further comprise a medium channel connected to the one or more controllably expandable base, wherein the medium comprises a gas, a liquid, or a mixture thereof (e.g., a vapor).

In any of the preceding embodiments, the body portion of the inner member can comprise walls defining an inner cavity and a nut inside the inner cavity, wherein the nut is securely fixed to the walls via one or more inner member arm. In some aspects, the body portion of the inner member further comprises one or more longitudinal slit. In some aspects, the outer member comprises one or more outer member arm through the one or more longitudinal slit of the inner member, wherein the one or more outer member arm is connected to a screw engaging or configured to engage the nut, thereby connecting or configured to connect the outer member and the inner member. In some aspects, the screw and/or the nut is connected to a motor capable of effecting relative rotation of the screw and the nut, thereby effecting the sliding movement between the outer member and the inner member. In any of the preceding embodiments, the one or more longitudinal slit can be configured to prevent the inner member and the outer member from becoming disconnected during the sliding movement.

In any of the preceding embodiments, the device can further comprise a controllably expandable structure configured to expand or contract longitudinally, thereby effecting the sliding movement between the outer member and the inner member. In some aspects, the controllably expandable structure is distal to the first controllably expandable element, wherein longitudinal expansion and/or contraction of the controllably expandable structure effects a longitudinal movement of the first controllably expandable element relative to the second controllably expandable element. In some aspects, the controllably expandable structure is proximal to the first controllably expandable element, wherein longitudinal expansion and/or contraction of the controllably expandable structure effects a longitudinal movement of the first controllably expandable element relative to the second controllably expandable element. In some aspects, the device comprises two controllably expandable structures, one of which is distal to the first controllably expandable element while the other one is proximal to the first controllably expandable element, wherein coordinated longitudinal expansion and/or contraction of the two controllably expandable structures effects a longitudinal movement of the first controllably expandable element relative to the second controllably expandable element. In some aspects, the controllably expandable structure is distal to the second controllably expandable element, wherein longitudinal expansion and/or contraction of the controllably expandable structure effects a longitudinal movement of the first controllably expandable element relative to the second controllably expandable element. In some aspects, the controllably expandable structure is proximal to the second controllably expandable element, wherein longitudinal expansion and/or contraction of the controllably expandable structure effects a longitudinal movement of the first controllably expandable element relative to the second controllably expandable element. In some aspects, the device comprises two controllably expandable structures, one of which is distal to the second controllably expandable element while the other one is proximal to the second controllably expandable element, wherein coordinated longitudinal expansion and/or contraction of the two controllably expandable structures effects a longitudinal movement of the first controllably expandable element relative to the second controllably expandable element. In some aspects, the controllably expandable structure is between the first controllably expandable element and the second controllably expandable element, wherein longitudinal expansion and/or contraction of the controllably expandable structure effects a longitudinal movement of the first controllably expandable element relative to the second controllably expandable element.

In any of the preceding embodiments, the controllably expandable structure can comprise or be a telescoping balloon. In any of the preceding embodiments, the controllably expandable structure can comprise or be a shape-memory alloy, e.g., a spring made of a shape-memory alloy. In any of the preceding embodiments, the controllably expandable structure can comprise or be a compliant balloon and/or a semi-compliant balloon. In any of the preceding embodiments, the controllably expandable structure can comprise or be a bellows, e.g., a compliant bellows.

In any of the preceding embodiments, the device can further comprise a plurality of controllably expandable structures between the first controllably expandable element and the second controllably expandable element, wherein expansion and/or contraction of the plurality of controllably expandable structures effects a longitudinal movement of the first controllably expandable element relative to the second controllably expandable element. In some embodiments, the plurality of controllably expandable structures form a helix. In any of the preceding embodiments, expansion and/or contraction of the plurality of controllably expandable structures effects a rotational movement of the first or second controllably expandable element relative to each other. In some aspects, the first or second controllably expandable element is in a contracted or deflated state during the rotational movement. In any of the preceding embodiments, the device can further comprise two, three or more controllably expandable structures. In any of the preceding embodiments, expansion and/or contraction of the plurality of controllably expandable structures effects articulation of a distal portion of the inner and/or outer member in a direction transverse to the longitudinal axis of a body portion of the inner and/or outer member.

In any of the preceding embodiments, the controllably expandable structures can comprise one or more compliant balloon and/or one or more semi-compliant balloon. In any of the preceding embodiments, the controllably expandable structures can comprise one or more bellows, e.g., a compliant bellows. In some aspects, the plurality of controllably expandable structures comprise two or more pressure balloons. In some aspects, the plurality of controllably expandable structures comprise a pressure balloon, a pressure chamber, or combinations thereof. In some aspects, the plurality of controllably expandable structures comprise three or four pressure balloons. In some aspects, the plurality of controllably expandable structures comprise three or four pressure chambers. In any of the preceding embodiments, a subset of the plurality of controllably expandable structures can be configured to selectively inflate and/or deflate, thereby effecting articulation of the second controllably expandable element in a direction transverse to the longitudinal axis of the outer member.

In any of the preceding embodiments, the device can further comprise a plurality of controllably expandable structures distal to the second controllably expandable element, wherein a subset of the plurality of controllably expandable structures are configured to selectively inflate and/or deflate, thereby effecting articulation of the distal end of the inner member in a direction transverse to the longitudinal axis of the outer member.

In any of the preceding embodiments, the first controllably expandable element can comprise a plurality of treads on a surface configured to engage the wall of the body cavity. In any of the preceding embodiments, the second controllably expandable element comprises a plurality of treads on a surface configured to engage the wall of the body cavity.

In some aspects, disclosed herein is a method for locomotion of the device disclosed in any of the embodiments herein through a body cavity. In some aspects, the method comprises i. expanding the second controllably expandable element radially outwardly to engage a wall of the body cavity, optionally while the first controllably expandable elements is not radially outwardly expanded, thereby fixing the second controllably expandable element to a first position in the body cavity; ii. effecting sliding movement between the outer member and the inner member to retract the distance between the first and second controllably expandable elements; iii. expanding the first controllably expandable element radially outwardly to engage a wall of the body cavity; iv. contracting the second controllably expandable elements radially and inwardly; v. effecting sliding movement between the outer member and the inner member to extend the distance between the first and second controllably expandable elements; and vi. expanding the second controllably expandable element radially outwardly to engage a wall of the body cavity, optionally while the first controllably expandable elements is not radially outwardly expanded, thereby fixing the second controllably expandable element to a second position in the body cavity. In some embodiments, the method further comprises repeating steps of ii-vi.

In any of the preceding embodiments, the method can further comprise delivering a substance into the body cavity through one or more channel of the inner member. In any of the preceding embodiments, the method can further comprise removing a substance from the body cavity through one or more channel of the inner member. In any of the preceding embodiments, the method can further comprise capturing an image of the body cavity through one or more channel of the inner member. In any of the preceding embodiments, the method can further comprise performing an operation of a tissue within the body cavity through one or more channel of the inner member.

In any of the preceding embodiments of the device or method disclosed herein, the body cavity can be a vascular body lumen, a digestive body lumen, a respiratory body lumen, or a urinary body lumen. In some aspects, the digestive body lumen is a gastrointestinal tract. In some aspects, the gastrointestinal tract is small intestine. In some aspects, the gastrointestinal tract is duodenum, jejunum, or ileum. In some aspects, the gastrointestinal tract is colon. In some aspects, the gastrointestinal tract is esophagus. In some aspects, the gastrointestinal tract is stomach.

DETAILED DESCRIPTION

Figure 1A:
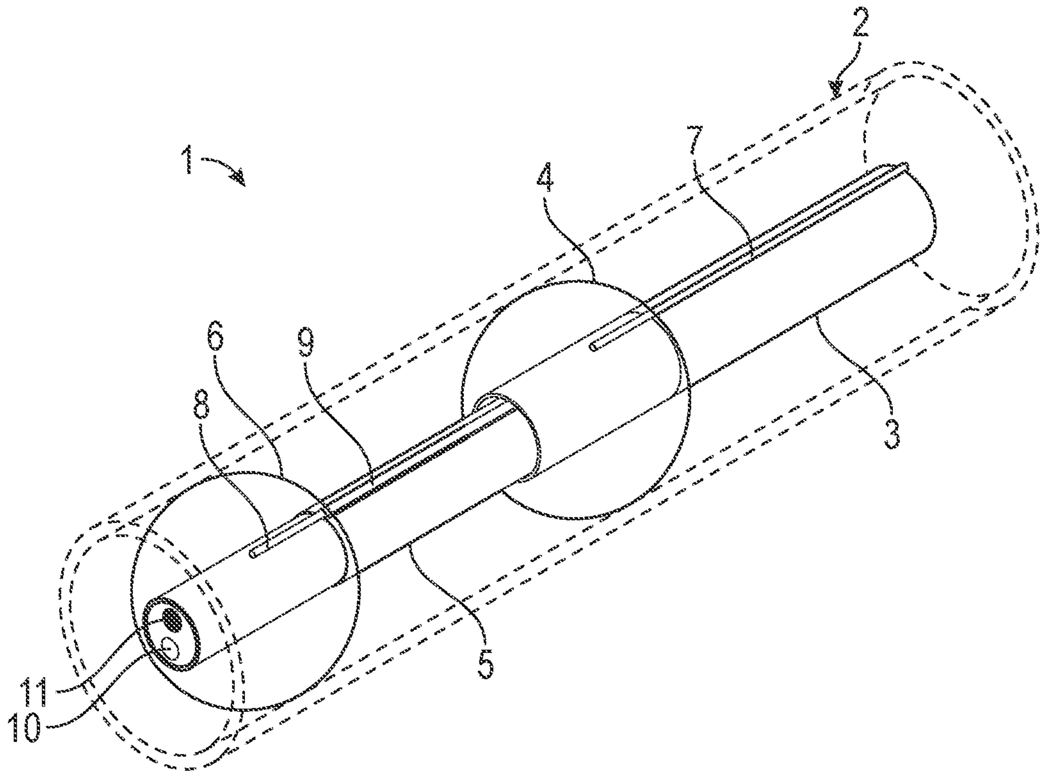
FIGS. 1A-1D show the structure and application of an exemplary device comprising two controllably expandable elements, an outer tube, an inner tube, a connector, and an actuator.
Figure 1B:
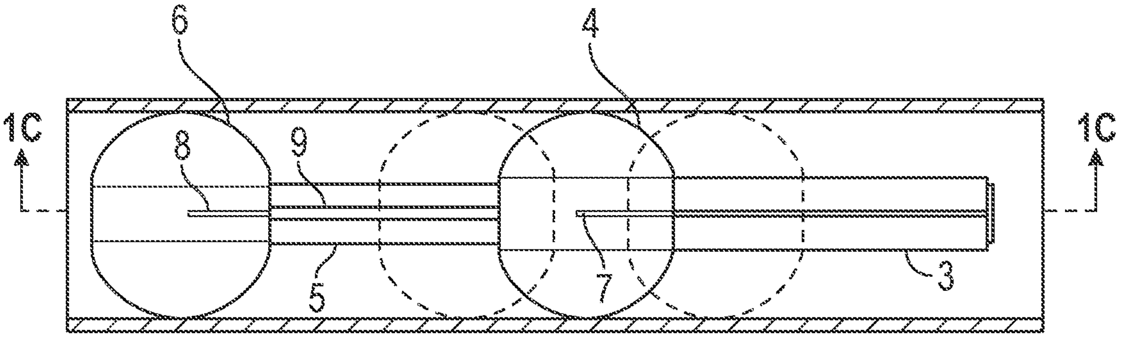
Figure 1C:
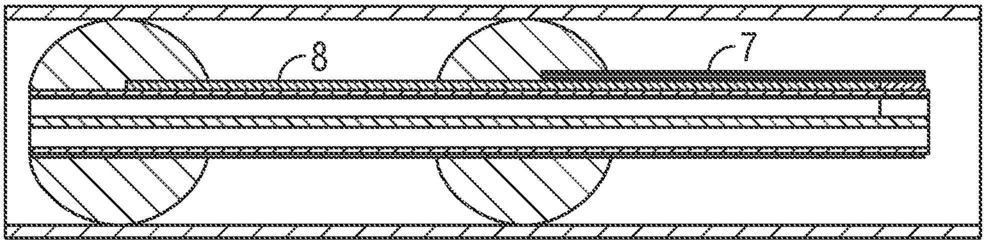

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. All publications, including patent documents, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

Provided herein is a device configured to move within a body cavity. In some embodiments, the device comprises a double-balloon system comprsing an actuating or driving mechanism, as well as an articulation mechanism to navigate the complicated curves of a body cavity such as the GI tract. The device may be used but is not made exclusively for enteroscopy. It can be used in any part of the gastrointestinal tract. For example, the device may be used as a colonoscope for technically difficult cases. The device may be used for endoscopic retrograde cholangiopancreatography, e.g., in patients with Roux-en-Y anastomosis in which an endoscopic approach to the papilla of Vater is impossible with regular endoscopic insertion. In some embodiments, the present device provides not only improved accessibility to a distal portion of the GI tract, e.g., the small intestine.

In some embodiments, the present device provides not only improved accessibility to the deep small intestine, but also the ability to control the device tip in any part of the intestine. Precise control of the device tip is possible at any point in the intestine because the movement of the device is controlled from the gripped point by the balloon on the inner tube and/or the balloon on the outer tube, which can be set at any point.

In some embodiments, the present device may be used in place of or in conjunction with a traditional capsule endoscopy and/or balloon-based. Capsule endoscopy is suitable for the initial work-up of nonobstructive small intestinal disorders because it is discomfort-free and does not require the patient to be confined to a medical facility. Abnormal findings detected by a capsule can be confirmed by the presently disclosed device with biopsy examination, and endoscopic treatment can be performed using the device disclosed herein. In particular, small intestinal strictures, which are a contraindication for capsule endoscopy, can be explored by the device disclosed herein. In some embodiments, the device disclosed herein may be used to perform endoscopic balloon dilation. Moreover, in cases of capsule retention at a stricture, the capsule can be retrieved by the device disclosed herein and the stricture can be dilated endoscopically using the device.

In some embodiments, provided herein is a gastrointestinal (GI) navigation and delivery device. In some aspects, the device is designed to navigate through the gastrointestinal system with no or much less human manipulation during the navigation, as compared to conventional endoscopy. In some embodiments, the device is a self-driving device. In some embodiments, the device minimizes or ends the need for sedation. In some embodiments, the device also cuts the procedural cost that is associated with supporting staff, medical supplies, medications, and hospital stay.

In some embodiments, provided herein is a gastrointestinal navigation and delivery device capable of delivering medication to one or more target region within a body cavity. In some embodiments, provided herein is a device configured to deliver an endoscope, a diagnostic capsule, a diagnostic catheter such as a manometry catheter, a therapeutic device such as a stent, a tube, and other device or composition to one or more desired region within a body cavity.

In some embodiments, provided herein is a device configured to drive a capsule endoscopy for the small bowel and colon through the GI tract with a controlled speed and direction. In some embodiments, the device disclosed herein is configured to carry the task for bowel preparation, which is a very unpleasant process and the huge obstacle for people to adhere to colon cancer screening recommendation.

In one aspect, provided herein is a lumen navigation and delivery device comprising a first body section with a proximal end and a distal end, a second body section with a proximal end and a distal end, and a tip section with a proximal end and a distal end wherein the proximal end of the tip section is attached to the distal end of the second body section and the first and second body sections are attached to and capable of sliding within one another in a telescopic fashion. In some embodiments, the first body section, the second body section, and the tip section each comprise a tubular structure.

In some embodiments, the first body section is larger in size than the second body section such that the second body section is capable of sliding within the first body section. In other embodiments, the second body section is larger in size than the first body section such that the first body section is capable of sliding within the second body section.

In certain embodiments, an inflatable balloon is fixed to the outer wall of the proximal end of the outer tube. In some embodiments, one or more annular inflatable balloons are fixed to the outer wall of the proximal end of the outer tube. In particular embodiments, two spherical inflatable balloons are fixed opposite one another to the outer wall of the proximal end of the outer tube. In certain embodiments, a plurality of spherical inflatable balloons are attached, fixed in position relative to one another, to the outer wall of the proximal end of the outer tube and are arranged substantially evenly in a circular pattern to form an annular-like configuration around the outer tube.

In certain embodiments, an inflatable balloon is fixed to the outer wall of the distal end of the tip section of the inner tube. In some embodiments, one or more annular inflatable balloons are fixed to the outer wall of the distal end of the tip section of the inner tube. In particular embodiments, two spherical inflatable balloons are fixed opposite one another to the outer wall of the distal end of the tip section of the inner tube. In certain embodiments, a plurality of spherical inflatable balloons are attached, fixed in position relative to one another, to the outer wall of the distal end of the tip section and are arranged substantially evenly in a circular pattern to form an annular-like configuration around the tip section.

In certain embodiments, the inflation and deflation of the balloons are controlled by the injection of fluid. In some embodiments, fluid to each balloon is delivered via one or more channels fixed along the outer and inner tubes. In particular embodiments, the one or more channels delivering fluid to the balloons attached to the first tube are fixed to the outer wall of the first tube. In some embodiments, the one or more channels delivering fluid to the balloons attached to the first tube are fixed to the inner wall of the first tube. In some embodiments, the one or more channels delivering fluid to the balloons attached to the inner tube is fixed to the outer wall of the inner tube. In some embodiments, the one or more channels delivering fluid to the balloons attached to the inner tube is fixed to the inner wall of the inner tube.

In certain embodiments, the balloons are made of a material with memory of desired shapes. In some embodiments, the balloons will have a pre-set maximum pressure. In particular embodiments, the balloons incorporates certain adhesive properties. In certain embodiments, the balloons incorporate microfibrillar adhesives from polydimethylsiloxane.

In some embodiments, the gastrointestinal navigation and delivery device disclosed herein comprises an inner tube and an outer tube. In some embodiments, the inner tube moves forward to reach its distance, and may be anchored on the bowel wall by inflating the balloon at the distal end of the inner tube. Then, the outer tube follows by moving forward over the inner tube. Once the outer tube is in place, it is anchored on the bowel wall by inflating the balloon at the proximal end of the outer tube. At this time, the balloon on the inner tube is deflated and moves forward. Once the inner tube reaches its distance, the balloon on the inner tube advances to a more distal position within the body cavity such as the GI tract. Then, the inner tube is anchored onto the bowel wall by inflating its associated balloon, and the outer tube deflates its associated balloon to move forward over the inner tube. The process continues until it reaches a destination, such as a more distal desitantion in the GI tract, e.g., the small intestine.

In any of the embodiments disclosed herein, the balloons can be made of a material that has memory of the desired shape. In any of the embodiments disclosed herein, the balloons can incorporate certain adhesive properties such as microfibrillar adhesives (e.g., from polydimethylsiloxane (PDMS)) to generate traction. In any of the embodiments disclosed herein, the balloons can have a pre-set maximum pressure (thus maximum inflaction) and memory to prevent trauma to bowel wall or cause bowel perforation. In any of the embodiments disclosed herein, the balloons can be circumferentially wrapping around the inner and/or outer tubes. In any of the embodiments disclosed herein, the device can comprise multiple balloons at the same longitudinal position.

In any of the embodiments disclosed herein, the inflation and/or deflation of the balloons may be controlled, for example, by injecting and/or drawing a gas (such as air) or a fluid via thin tubing along the inner and outer tubes, respectively. In some embodiments, there is provided a tube or an air channel that is along the outside of the outer or inner tube or inside the outer or inner tube, for each balloon, respectively. In some embodiments, there is provided a tube or an air channel that is along the outside of the outer or inner tube for each balloon, respectively. In some embodiments, there is provided a tube or an air channel that is inside the outer or inner tube, for each balloon, respectively. In some embodiments, a part of the tube or air channel is along the outside of the outer or inner tube, while another part of the tube or air channel is inside the outer or inner tube, for each balloon, respectively.

In some embodiments, the device comprises a structure similar to screw and nut, for the inner and outer tubes to move relative to each other. In some embodiments, the screw is inside the inner tube but connected to the outer tube via a stepper motor. An exemplary stepper motor is the commercially available SM3.4-20 from Minebea or vendors. In some embodiments, the stepper motor connects to the outer tube via two arms. In some embodiments, the inner tube connects to a nut which is fixed onto the inner tube. In some embodiments, the nut moves along the screw. In some embodiments, the rotation of the screw enables the nut and the inner tube to move along the outer tube. In some embodiments, with the nut and/or screw moving in one direction and the outer tube being kept stationary by its balloon, the inner tube moves forward; with the nut and/or screw moving in the other direction, and when the inner tube is kept stationary by its balloon, the outer balloon moves forward. Using the same mechanism, both tubes can also move backwards. In some embodiments, the stepper motor connects to a proximal end of the screw to provide the movements. In some embodiments, the stepper motor are connected to the proximal portion of the outer tube via two arms that are fixed onto the outer tube.

In some embodiments, a plurality of longitudinal slits are located on the walls of the inner tube. For example, two longitudinal slits may be provided on the opposite walls of the inner tube. In some embodiments, two arms extend from stepper motor for the screw through the slits and are fixed onto the outer tube. In some embodiments, the plurality of longitudinal slits provide space for the inner tube and outer tube to slide forward and backward, while slidably connecting the inner tube and outer tube during the movements, e.g., in order to prevent the two tubes from disengaging each other (e.g., the distal portion of the inner tube may slide completely into the outer tube or the inner tube may slide completely outside the outer tube) and/or control the maximum/minimum distance between the two balloons, during alternating extensions and retractions of the distance between the two balloons.

In some embodiments, the moving mechanism is advantageous over the current endoscopy in that the device drives itself forward instead of an operator pushing it forward from outside of the body a long distance away. In some embodiments, the mechanism avoids the stretching of the bowel, bowel wall and mesentery, thereby decreasing pain and consequently requiring less sedation and operation time.

In some embodiments, the distal end of the inner tube has an opening for camera. In some embodiments, the device comprises a camera at least part of which is in the inner tube. In some embodiments, the device comprises a light source, e.g., a light source for the camera. In some embodiments, the distal end of the inner tube has an opening for air and/or water. In some embodiments, the distal end of the inner tube has an opening for an irrigation and/or suction channel. In some embodiments, the inner tube can be tapered down in diameter if needed toward the distal end, especially when only an opening for camera and an opening or an irrigation and/or suction channel are needed. In some embodiments, the camera can be a fiber optic camera such as a miniature CMOS image sensor (e.g., NanEye by AMS AG), a camera used in capsule endoscopy, or a wireless camera that is often used in mini drones. In some embodiments, the very distal end of the inner tube is oval or round in shape to minimize trauma to the bowel wall.

In some embodiments, the inner tube comprises two portions, a distal tip portion and a proximal body portion. In some embodiments, the proximal end section of the inner tube tip is connected to the body of inner tube via a motor. In some embodiments, the motor is at a proximal end of the tip portion (and/or at a distal end of the body portion) and connected to a around base that can be inflated and/or deflated to form an asymmetrical shape. In some embodiments, the asymmetrically inflated base enables the tilting of the tip. In some embodiments, the base can rotate in 360 degree fashion that is controlled by another motor, for example, a servo motor or a stepper motor. In some embodiments, by combining the base rotation and tilting the tip, the tip portion of the inner tube is capable of guiding the inner tube to move in various directions. This feature is advantageous for navigating the GI tract, particularly the small intestine.

In some embodiments, the round base is a flexible conduit-like structure, except it is asymmetrical and has a hinge at one side. The hinge can be an actual hinge, such as a mechanical hinge with two parts that pivot relative to each other. In some embodiments, the hinge can be an extension from the distal section of the inner tube that is made of a material that is strong enough and yet can be bent repeatedly.

In some embodiments, the round base is a chamber that comprises a relatively rigid material (e.g., plastic) on both top and bottom surfaces and an elastic material with shape memories on the side. In some embodiments, the top surface (distal) of the round base is the base of the inner tube base. In some embodiments, the bottom surface (proximal) of the round base is separated from the distal surface of the inner tube body and connected with a motor, such as the servo or stepper motor which is connected with the body portion of the inner tube.

In some embodiments, the space between the round base and the distal surface of the inner tube body is small enough to allow the free rotation of the round base. In some embodiments, the chamber of the round base can maintain an angle from 0 degree to 180 degree at the hinge by inflating the base chamber. In some embodiments, if more than 90 degree at the hinge is needed, another chamber that is on top of the first one can be provided to share the same hinge with the first chamber. In some embodiments, in order to maintain an angle between 90 degree and 180 degree at the hinge, another chamber can be provided on top of the first one. In some embodiments, when the chamber returns to its original position with 0 degree at the hinge, there is still some room maintained between the top surface and the lower surface of the chamber. In some embodiments, the distance between the two surfaces depends on the thickness of the folded flexible conduit. In some embodiments, when the angle is at or at about 0 degree, the intra-chamber pressure can be maintained close to zero or even slightly negative to keep the tip of the inner tube and body of the inner tube as one unit.

In some embodiments, the inflation is achieved by a gas (such as sterilized air), a liquid or fluid, or a mixture thereof (such as vapor). In some embodiments, inside the round base, there is a thin cuboid shaped chamber that can be inflated asymmetrically to a triangular shape, thereby inflating the round base to a desired angle. In some embodiments, the cuboid shaped chamber extends across a diameter of the round base but leaves space for one or more flexible tube, e.g., for the air/water/suction channel and the camera cable to pass through the round base. In some embodiments, there is an air channel going through the inner tube body and connect to the round base via a flexible conduit. In some embodiments, regulation of the inflation and rotation of the round base is achieved by a computer program that receives feedback from device, such as from the camera or a sensor, such as a pressure sensor at the tip of the inner tube. Therefore, in coordination with the camera or sensor at the tip of the inner tube, the inner tube recognizes the direction of the bowel lumen and guides the direction of the tube movements.

In some embodiments, the motor on the round base is a servo motor that has a sufficiently small size. In some embodiments, a stepper motor is used, or the servo motor can be placed proximal to the first stepper motor for the screw/nut and connected to the round base with a stiff thin wire that can accurately transmit servo motor's rotation to a pin on the round base via one or more gear.

In some embodiments, the water/air/suction channel is a channel traversing the whole inner tube from the proximal inner tube, round base to the distal inner tube. In some embodiments, there is a flexible tube that is fixed to the proximal end of the channel at the distal (tip) section of the inner tube and end freely in the air channel of the inner tube body but fits tightly in the air channel of the inner tube body to maintain a seal. In some embodiments, the flexible tube traverses the round base down to the inner tube body at a length that is long enough to still remain in the tube body's air channel when the round base is inflated to its largest angle at the hinge and when the round base rotates up to 180 degree to both directions (clockwise and counter-clockwise). In some embodiments, the flexible tube is made from a flexible material but does not collapse during operation or is capable to withstand a threshold pressure. In some embodiments, the air channel remains open when the round base is collapsed. In some embodiments, a fiber optic camera such as NanEye is used, the optical fiber can traverse the entire inner tube and/or traverse the round base in the closed relationship to the pin of the servo or stepper motor on the side of the hinge. In some embodiments, this configuration ensures the length of the cable that moves when the round base is rotating is minimum. In some embodiments, the camera cable is secured at the proximal end of the distal inner tube for the same reason as the tube inside the air channel. In some embodiments, a wireless camera is used, and the length of the camera cable that moves when the round base is rotating is not a concern. In some aspects, the air/water irrigation/suction channel and the fiber optic camera traverse the round base through an air-sealed tunnel, for example, to ensure that the round base is air sealed.

In some embodiments, the inner tube body and the outer tube are relatively larger in diameter, while the rest of the inner tube distally has a smaller diameter, for example, carrying only the air/water/suction channel and/or wires (e.g., electric wires for the camera and/or one or more motor). In some embodiments, the electric wires connect the camera and/or motor to a control mechanism outside of the body of a subject.

In some embodiments, the device further comprises a guidewire attached to the outer tube distally and to the inner tube proximally, for example, as a carrier system that allows other mechanisms, such as sample collection, imaging collection, data analysis, delivery of one or more scope and/or catheters etc., to feed over the guidewire and be delivered to a desired location.

In any of the preceding embodiments, the device described herein is configured to move and/or navigate inside a body cavity, such as for intra-vascular or intra-luminal use in other organ systems, e.g., in the respiratory system or the urinary tract.

In some embodiments, provided herein is a controllably expandable structure for use in the device described herein. In some embodiments, the controllably expandable structure (e.g., an inflatable element such as a balloon-type element) is configured to expand from a collapsed configuration to an expanded configuration, wherein, when in the collapsed configuration, the controllably expandable structure includes one or more fold or ridge extending substantially transverse to a longitudinal axis thereof so that, when a medium (e.g., a gas, a liquid, or a mixture thereof such as a vapor) is supplied thereto, e.g., for inflation, the controllably expandable structure expands substantially along the longitudinal axis. In some embodiments, the controllably expandable structure is connected to an actuator (e.g., an actuator for surgical or endoscopic applications), e.g., via a medium conduit or channel (e.g., an inflation gas/fluid/vapor conduit) or via mechanical structures (such as rods or gears).

In some embodiments, the actuator forms an integral part of the device and remains inside a patient's body during operation of the device. Exemplary actuators include miniaturized motors coupled to the controllably expandable structure, e.g., via the medium conduit or channel and/or mechanical structures.

In some embodiments, the actuator remains outside a patient's body, and the medium conduit or channel extends from the actuator to a proximal end of the controllably expandable structure, thereby coupling the actuator and the controllably expandable structure. In some embodiments, when the actuator is in a first operative configuration, a medium such as an inflation gas, fluid, or vapor is supplied to the controllably expandable structure via the medium conduit or channel. In some embodiments, when the actuator is in a second operative configuration, a medium such as an inflation gas, fluid, or vapor is withdrawn from the controllably expandable structure via the medium conduit or channel. In some embodiments, when the actuator is in a third operative configuration, a certain amount of a medium such as an inflation gas, fluid, or vapor is maintained in the controllably expandable structure, thereby maintaining the state and/or degree of expansion of the controllably expandable structure. In some embodiment, there is no net change of the amount of the medium inside the controllably expandable structure when its degree of expansion is maintained.

In any of the preceding embodiments, the controllably expandable structure may comprise a compliant balloon, a non-compliant balloon, and/or a semi-compliant balloon. The term "compliance" as it relates to balloons describes the degree to which the size of a balloon changes as a function of pressure. Compliant balloons exhibit substantially uniform expansion in response to increasing levels of pressure. A compliant balloon may be "axially compliant" and have a length that exhibits uniform axial expansion during inflation of the balloon; "radially compliant" and have a radius that exhibits uniform radial expansion during inflation of the balloon; or both. Compliant balloons are made of materials that are highly elastic and expand substantially elastically when pressurized. These materials may also have substantial elastic recoil such that upon deflation, compliant balloons return substantially to their original pre-inflation size. Compliant balloon materials include thermosetting and thermoplastic polymers that exhibit substantial stretching upon the application of tensile force. These materials include, but are not limited to, elastomeric materials such as elastomeric varieties of latex, silicone, polyurethane, and polyolefin elastomers. See for example U.S. Pat. No. 7,892,469, which is incorporated herein by reference in its entirety and for all purposes. Compliant balloon materials may be cross-linked or uncross-linked.

Non-compliant balloons, on the other hand, exhibit little expansion in response to increasing levels of pressure. A non-compliant balloon may be "axially non-compliant" and have a length that exhibits little or no axial growth during inflation of the balloon; "radially non-compliant" and have a radius that exhibits little or no radial growth during inflation of the balloon; or both. In the case of a radially non-compliant balloon, the walls of the balloon when uninflated may collapse into folded pleats, allowing the balloon to adopt an axially compressed state. Upon inflation, these pleats unfold, and the axial length of the balloon grows as the radius of the balloon remains substantially unchanged. Non-compliant balloon materials include, but are not limited to, nylon, polyethyleneterephthalate (PET), or various types of polyurethane block copolymers. See Lim et al. Non-compliant balloons can be used to open or expand a body lumen, and due to their predetermined size, they are less likely than compliant balloons either to burst or to rupture or damage lumen walls when highly pressurized. See for example U.S. Pat. No. 8,469,926, which is incorporated herein by reference in its entirety and for all purposes.

In some embodiments, semi-compliant balloons exhibit moderate expansion in response to increasing levels of pressure. In some embodiments, in response to increasing inflation pressure, a semi-compliant balloon expands less than a compliant balloon, but more than a non-compliant balloon. A non-compliant balloon may be "axially semi-compliant," "radially semi-compliant," or both. Thus, in some embodiments, with the same pressure, different parts of a semi-compliant balloon may exhibit different degrees of expansion. In other words, a semi-compliant balloon may be designed to expand in more than one direction, but with different degrees of expansion in different directions.

As with non-compliant balloons, semi-compliant balloons may be made of materials that include, but are not limited to, nylon, polyethyleneterephthalate (PET), or polyurethane block copolymers. Semi-compliant balloons maintain in part at least some of the advantages of non-compliant balloons detailed above, but also preserve at least some of the elasticity and flexibility of compliant balloons.

Depending upon the nature of the operation, it may be desirable to further adjust the positioning of an end portion of the inner member and/or an end portion of the outer member. In some embodiments, it is desirable to orient a distal end portion of the inner member at an axis transverse to the longitudinal axis of a body portion of the device, such as a body portion of the inner tube. The transverse movement of the end portion relative to the body portion of the device may be referred to as "articulation." In some embodiments, articulation is accomplished by a pivot (or articulation) joint being placed between the end portion and the body portion. This articulated positioning permits an operator of the presently disclosed device to more easily engage tissue in some instances and/or navigate the device through a complicatedly curved body cavity, such as the GI tract. In combination of the self-driving mechanisms disclosed herein, the device may be used to gain access to deep parts that are complicatedly curved, such as the small intestine. In some embodiments, articulated positioning advantageously allows the end portion of the device to be positioned in the body cavity without being blocked by tissue inside the body cavity.

In some embodiments provided herein, the device comprises a hydraulic actuator in between the first controllably expandable element and the second controllably expandable element of the device, and engagement of the hydraulic actuator effects the sliding movement between the outer member and the inner member of the device. In other embodiments, mechanical actuators like lead screws or cable assemblies can be used instead. In some embodiments, the device further comprises a plurality of soft, compliant fluid channels running longitudinally through the device, and individual inflation and deflation of said channels with liquid or air effects the bending of the tip of the device.

In some embodiments provided herein, the device comprises a hydraulic articulation and propulsion mechanism. In some embodiments, the device may be driven by an articulation movement powered by hydraulic actuated flexible cylinders and/or rods to bend the tip of the device. For example, three hydraulically powered flex rods may enable the instrument to bend when individually extended/retracted with non-compressible fluid. The first controllably expandable element and the second controllably expandable element, e.g., balloons, may independently inflate and deflate to fasten the device to the interior walls of the GI tract while a propulsion mechanism utilizing a hydraulic or mechanically powered actuator in between the elements pushes and pulls the device through the intestines. Mechanisms including hydraulic actuators, lead screws, cable assemblies can be used for the propulsion movement.

In some embodiments provided herein, the device comprises a hydraulic actuator in between the first controllably expandable element and the second controllably expandable element of the device, and engagement of the hydraulic actuator effects the sliding movement between the outer member and the inner member of the device. In other embodiments, mechanical actuators like lead screws or cable assemblies can be used instead. In some embodiments, the device further comprises a plurality of flexible rods running longitudinally through the device, and individual extension and retraction of said rods with non-compressible fluid effects the bending of the tip of the device.

In some embodiments provided herein, the device comprises a cable-driven actuator in between the first controllably expandable element and the second controllably expandable element of the device, and engagement of the cable-driven actuator effects the sliding movement between the outer member and the inner member of the device. In other embodiments, hydraulic actuators or lead screws can be used instead. In some embodiments, the device further comprises additional cables running longitudinally through the device, the distal ends of said cables fixed in the tip of the device. The cables are coupled with a plurality of motor-pulley systems, and individual pulling and pushing of said cables by the motor-pulley systems effects the bending of the tip of the device.

In some embodiments provided herein, the device further comprises a plurality of closed loop cables running longitudinally through the device, the distal ends of said cables fixed in the tip of the device. The cables are coupled with a plurality of motor-pulley systems, and individual pulling and pushing of said cables by the motor-pulley systems effects the bending of the tip of the device. A flexible housing unit surrounds the cable assembly to contain the articulation mechanism.

In some embodiments provided herein, the device comprises a three phase servo motor actuator. In this embodiment, linearly oriented coils are energized in sequence to propel the balloon mechanism forwards and backwards. The device further comprises a bidirectional magnet installed on the balloon mechanism in order to integrate with the magnetic linear actuator.

In some aspects, provided herein is a device configured to move within a body cavity, said device comprising: an outer member comprising a distal end, a proximal end, a lumen between the distal end and the proximal end, and a first controllably expandable element; an inner member slidably disposed in the lumen of the outer member, wherein the inner member comprises a distal end, a proximal end, and a second controllably expandable element; a connector that connects the outer member and the inner member; and an actuating member comprising a plurality of balloons (e.g., pressure balloons, or axially compliant balloons), a plurality of bellows or unit bellows, and/or a plurality of pressure chambers, wherein the actuating member is capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity. In any of the preceding embodiments, the actuating member is also capable of effecting articulation of the distal portion of the inner tube in a direction transverse to the longitudinal axis of the body portion of the inner tube, for example, via selective or preferential inflation and/or deflation of one or more of the plurality of balloons, the plurality of bellows or unit bellows, and/or the plurality of pressure chambers.

Reference is now made to the figures, which describe certain elements or aspects of multiple embodiments of the present disclosure. The drawings are provided for illustrative purposes only and are not meant to be limiting.

FIGS. 1A-1D show an exemplary device disclosed herein comprising two controllably expandable elements. As shown in FIG. 1A, a distal portion of device 1 may be placed inside a body cavity 2 such as a gastrointestinal (GI) tract of a subject. The outer tube 3 (e.g., an overtube) comprises a distal end, a proximal end, a lumen between the distal end and the proximal end, and a first controllably expandable element 4 on an outer surface of the outer tube. The first controllably expandable element can be a balloon capable of expanding radially outwardly to engage a wall of the body cavity 2. The inner tube 5 is slidably disposed in the lumen of the outer tube 3, and comprises a distal end and a proximal end. The inner tube 5 further comprises, on an outer surface of the inner tube, a second controllably expandable element 6. The second controllably expandable element can be a balloon capable of expanding radially outwardly to engage a wall of the body cavity 2. The first and second controllably expandable elements 4 and 6 may be controllably inflated or deflated through medium channels 7 and 8, respectively. The medium in the channels may be a gas, a liquid, or a combination thereof (e.g., a vapor), and the channels may be protected by a shrink tube 9. The inner tube 5 may comprise one or more working channel 10 and/or one or more chamber or channel for camera 11. When the controllably expandable elements 4 and 6 are expanded, they may engage the body cavity wall at different positions, as shown in the side view and a cross-section of the distal portion of device inside the body cavity in FIG. 1B and FIG. 1C, respectively.

Figure 1D:
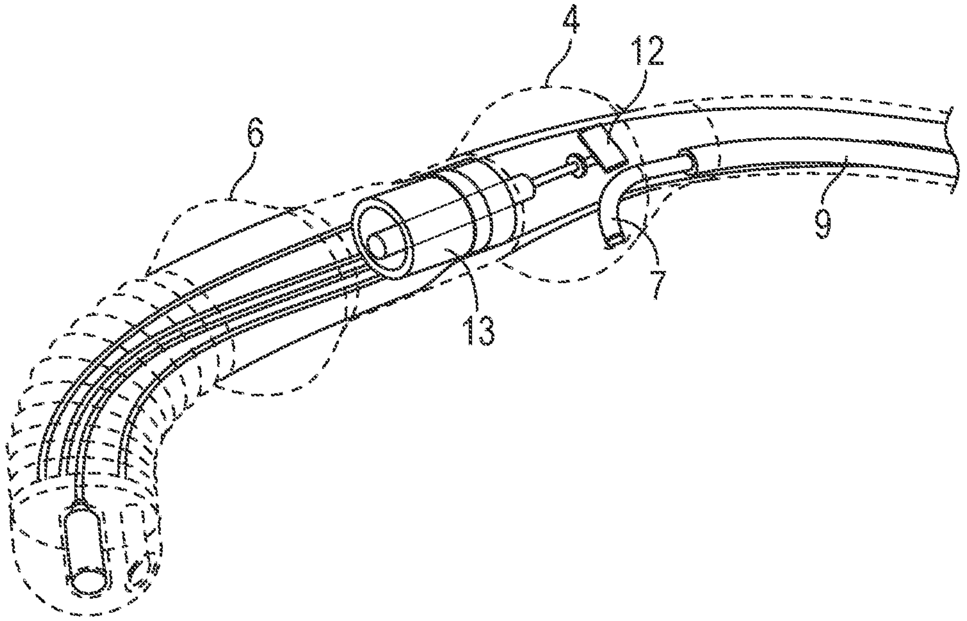

As shown in FIG. 1D, a connecting mechanism or connector 12 connects the outer tube 3 and the inner tube 5. An actuating mechanism or actuator 13 capable of effecting sliding movement between the outer tube 3 and the inner tube 5 is provided to alternate extensions and retractions of a distance between the balloon 4 and 6 along the length of the body cavity. The inner tube 5 may be inserted into the outer tube 3 under the condition that air is exhausted from the balloons 4 and 6 to deflate the balloons. The medium channel 7 providing a medium for inflating and/or deflating the balloon 4 is also shown, and the medium channel may be protected by the shrink tube 9. In preferred embodiments, the inner tube and the outer tube are pre-assembled, with the inner tube slidably placed inside the outer tube, before the distal portion of the device is placed inside the body cavity. In preferred embodiments, the inner tube and the outer tube are pre-assembled and connected to each other via a connecting mechanism, with the inner tube slidably placed inside the outer tube, before the distal portion of the device is placed inside the body cavity. Thus, there is no need for an operator to insert the inner tube through the outer tube during operation of the device.

The distal end of the device may be placed within the body cavity at an initial position proximal to the operator. In a retrograde (anal) approach, the initial position may be at a position in the rectum or colon, such as at the sigmoid colon, the descending colon, the transverse colon, or the ascending colon. In an anterograde approach, the initial position may be at a position in the esophagus, stomach, or small intestine, such as at the duodenum. Both balloons 4 and 6 may be completely deflated or in a less inflated state when placed at the initial position, and/or when the device is being placed at the initial position, for example, for ease of operation and patient comfort.

As an initial step, a remote control may be operated to supply a medium such as air from a pump outside the body of the subject to the balloon 4 attached in the distal end of the outer tube 3, thus inflating the balloon and fixing the balloon at the initial position. Consequently, the outer tube 3 is fixed to the initial position in the body cavity, such as the colon.

While the inflation state of the balloon 4 is maintained, sliding movement between the outer tube 3 and the inner tube 5 is actuated and optionally controlled by a control unit outside the body of the subject, to insert the inner tube 5 into a deeper part (e.g., more distal to the operator, e.g., the small intestine) of the body cavity, while the balloon 6 is deflated or in a less inflated state to permit the sliding movement. Consequently, the distance between the balloon 4 and 6 along the length of the body cavity becomes greater. After the inner tube 5 is inserted deeper by a distance, a remote control may be operated to supply a medium such as air from a pump outside the body of the subject to the balloon 6 attached in the distal end of the inner tube 5, thus inflating the balloon 6 and fixing the balloon at a more distal position. Consequently, the inner tube 5 is fixed to the more distal position, such as the small intestine.

The distance of the inner tube 5 movement may be a predetermined distance, or may be manually or automatically adjusted during operation. For example, a pressure sensor at the tip of the device may feed a detected pressure signal to a control unit outside the patient body, if the pressure sensed is over a certain threshold indicating stretching of the body cavity wall, thus the distance of inner tube advancement may be reduced or the articulation of the tip of the device may be adjusted, in order to eliminate or reduce stretching.

While the inner tube 5 is fixed at the more distal position, a remote control may be operated to exhaust air from the balloon 4, which becomes deflated or less inflated so as to permit movement of the outer tube within the body cavity to a more distal position. Sliding movement between the outer tube 3 and the inner tube 5 is once again actuated and optionally controlled by a control unit outside the body of the subject, to move the outer tube 3 more distally into the body cavity, while the balloon 6 is inflated and balloon 4 is deflated or less inflated. Consequently, the distance between the balloon 4 and 6 along the length of the body cavity becomes smaller, and both balloons are now positioned at a more distal portion of the body cavity compared to the initial position that is more proximal to the operator. A remote control may be operated to supply a medium such as air from a pump outside the body of the subject to the balloon 4 attached in the distal end of the outer tube 3, thus inflating the balloon and fixing the balloon at the more distal position. While the inflation state of the balloon 4 is maintained, sliding movement between the outer tube 3 and the inner tube 5 is once again actuated to insert the inner tube 5 into a deeper part of the body cavity, while the balloon 6 is deflated or in a less inflated state to permit the sliding movement. Operation steps described above can be repeated to advance a distal end of the device into deeper parts, such as from colon to the small intestine, from ileum to jejunum, from jejunum to duodenum, or from duodenum to stomach.

In an alternative initial step, a remote control may be operated to supply a medium such as air from a pump outside the body of the subject to the balloon 6 attached in the distal end of the inner tube 5, thus inflating the balloon and fixing the balloon at the initial position. Consequently, the inner tube 5 is fixed to the initial position in the body cavity, such as the colon.

While the inflation state of the balloon 6 is maintained, sliding movement between the outer tube 3 and the inner tube 5 is actuated and optionally controlled by a control unit outside the body of the subject, to advance the outer tube 3 into a deeper part (more distal to the operator) of the body cavity, while the balloon 4 is deflated or in a less inflated state to permit the sliding movement. After the outer tube 3 is advanced deeper by a distance, a remote control may be operated to supply a medium such as air from a pump outside the body of the subject to the balloon 4 attached in the distal end of the outer tube 3, thus inflating the balloon 4 and fixing the balloon. Consequently, the outer tube 3 is fixed to a position distal to its initial position. The distance between the balloon 4 and 6 along the length of the body cavity also becomes smaller The distance of the outer tube 3 movement may be a predetermined distance, or may be manually or automatically adjusted during operation.

While the outer tube 3 is fixed at the more distal position, a remote control may be operated to exhaust air from the balloon 6, which becomes deflated or less inflated so as to permit movement of the inner tube within the body cavity to a more distal position. Sliding movement between the outer tube 3 and the inner tube 5 is once again actuated and optionally controlled by a control unit outside the body of the subject, to move the inner tube 5 distally into the body cavity, while the balloon 4 remains inflated and balloon 6 is deflated or less inflated. Consequently, the distance between the balloon 4 and 6 along the length of the body cavity becomes greater. When balloon 6 reaches a more distal destination, a remote control may be operated to supply a medium such as air from a pump outside the body of the subject to the balloon 6 attached in the distal end of the inner tube 5, thus inflating the balloon and fixing the balloon at the more distal position. While the inflation state of the balloon 6 is maintained, sliding movement between the outer tube 3 and the inner tube 5 is once again actuated to advance the outer tube 3 into deeper part of the body cavity, while the balloon 4 is deflated or in a less inflated state to permit the sliding movement. Operation steps described above can be repeated to advance a distal end of the device into deeper parts, such as from colon to the small intestine, from ileum to jejunum, from jejunum to duodenum, or from duodenum to stomach.

In any of the preceding embodiments, the device disclosed herein may also be operated to move from a more distal part of a body cavity to a more proximal part of the body cavity. In other words, the device disclosed herein may also be operated to move backwards. In any of the preceding embodiments, the device disclosed herein may move forward and backward in the body cavity, in any suitable combination or order, according to medical needs.

Figure 2A:
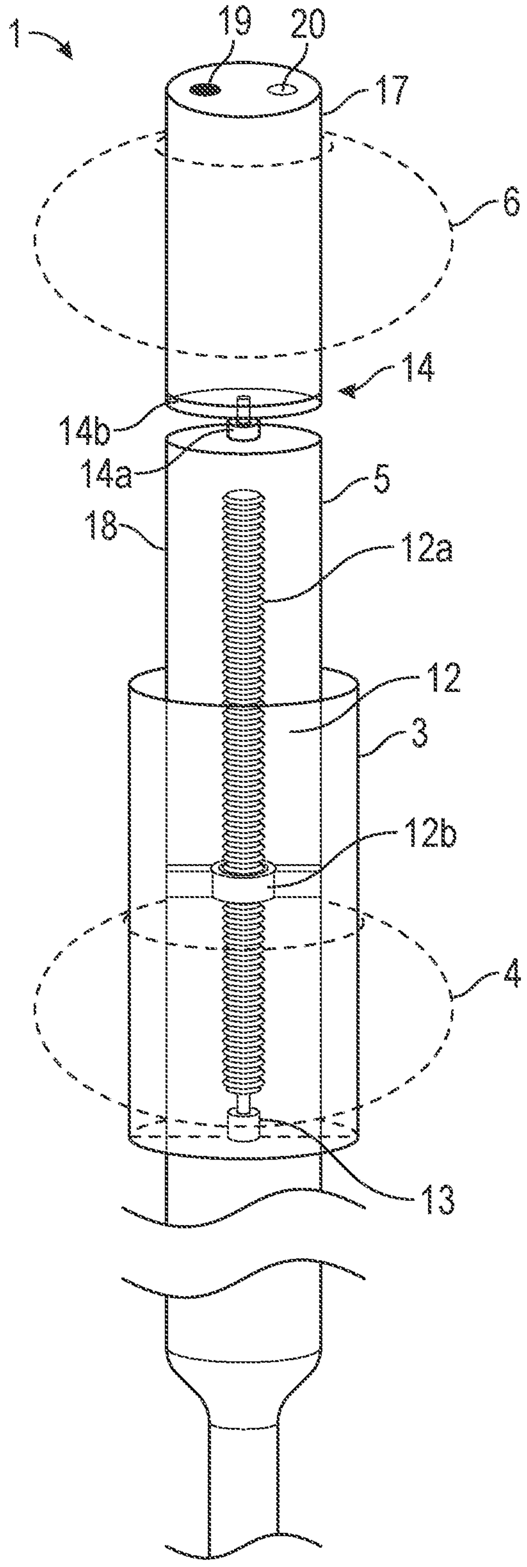
FIGS. 2A-2C show an exemplary device comprising an inner tube, an outer tube, two controllably expandable elements (e.g., balloons), a screw/nut connector, an actuating mechanism (e.g., a stepper motor), and an articulation mechanism.
Figure 2B:
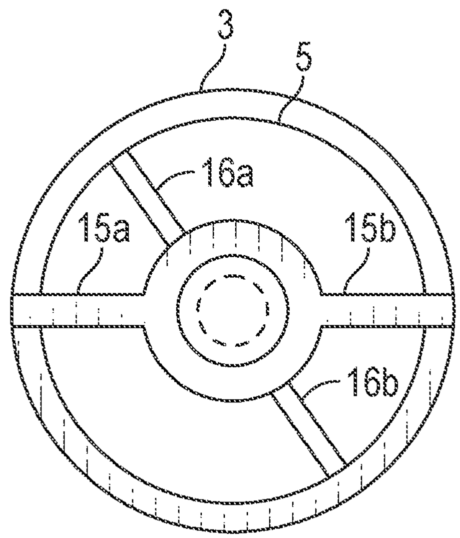
Figure 2C:
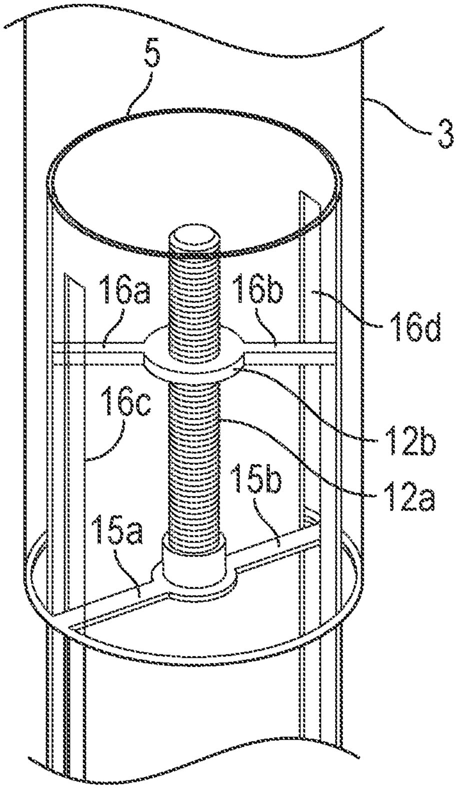

FIGS. 2A-2C show an exemplary device disclosed herein comprising an inner tube 5 and an outer tube 3, two controllably expandable elements (e.g., balloons) 6 and 4 on the inner tube and the outer tube, respectively, a screw/nut connector 12 and actuating mechanism 13, and an articulation mechanism 14. As shown in FIG. 2A, the device 1 comprises a screw 12*a* and a nut 12*b*, for the inner and outer tubes to move relative to each other. The screw 12*a* is inside the inner tube but connected to the outer tube via a motor 13, such as a stepper motor. The motor may be connected to a proximal portion of the outer tube as shown in FIG. 2A. The motor connects to the outer tube 3 via two arms 15*a* and 15*b*, which as shown in FIG. 2B are fixed onto the outer tube. The inner tube 5 connects to the nut 12*b* which is fixed onto the inner tube via two arms 16*a* and 16*b*. The rotation of the screw 12*a* enables the nut 12*b* and the inner tube 5 to move along the outer tube 3. When balloon 4 keeps the outer tube 3 (and the arms connecting to the motor) stationary, the inner tube 5 can move forward when the screw/nut moves in one direction and backward when the screw/nut moves in the opposit direction. When balloon 6 keeps the inner tube 5 (and the nut fixed thereto) stationary, the outer tube 3 can move forward and backward as well. FIG. 2C shows two longitudinal slits 16*c* and 16*d* on opposite walls of the inner tube 5. The two arms 15*a* and 15*b* extending from the motor 13 pass through the slits and are fixed onto the outer tube 3.

Referring again to FIG. 2A, the inner tube 5 comprises two portions, a distal end portion 17 and a proximal body portion 18. The distal end portion has an opening 19 for a camera and an opening 20 for air and/or water, e.g., as an opening for an irrigation and/or suction channel. The proximal end section of the inner tube distal end portion 17 comprises the base 14*b* which is connected to the body portion 18 via the motor 14*a*.

Figure 3:
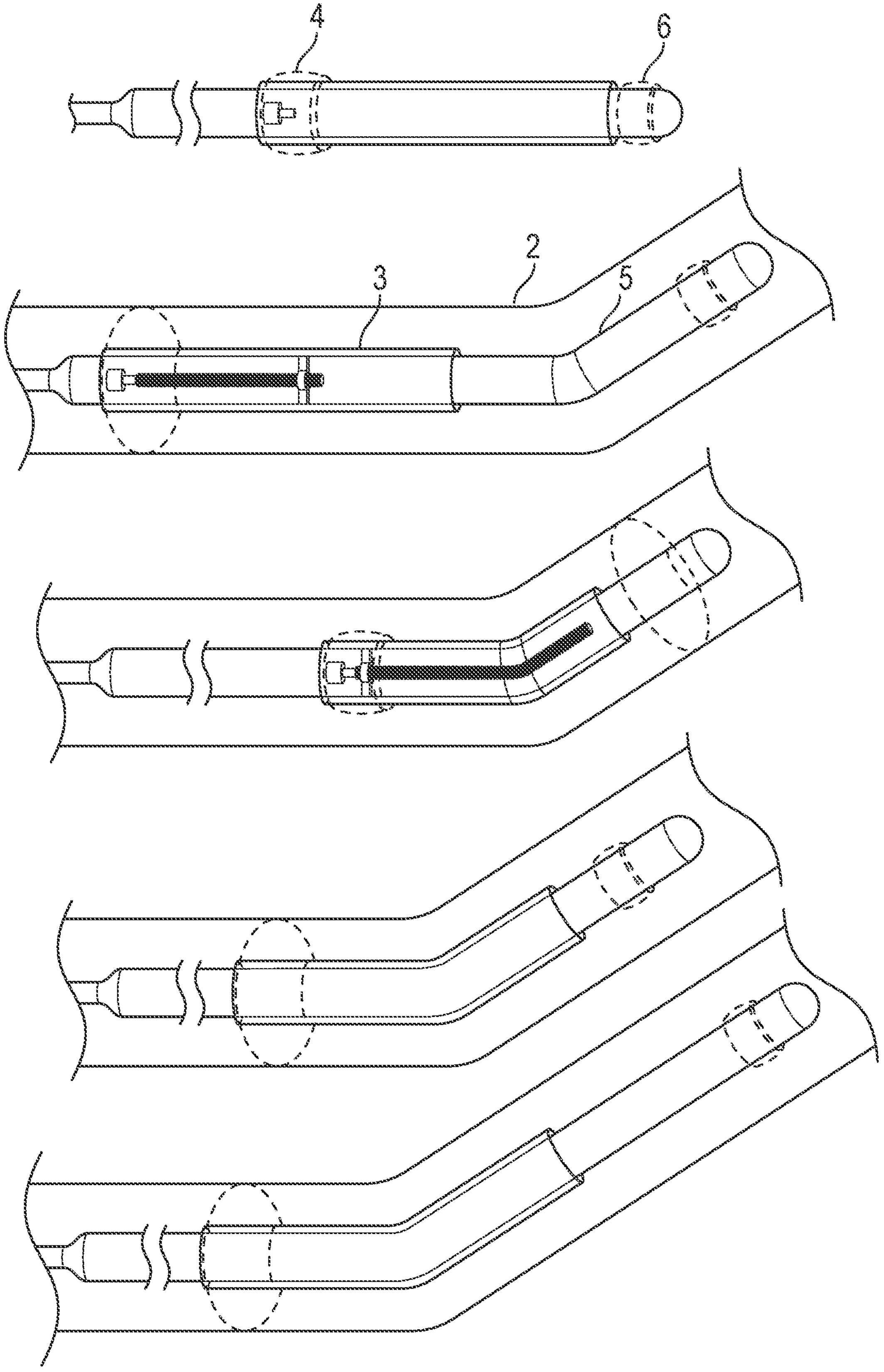
FIG. 3 shows an exemplary process of using a device disclosed herein, including the placement and movement of the device inside a body cavity such as a gastrointestinal tract.

As shown in FIG. 3, both balloons 4 and 6 are deflated before and when the device is placed inside the GI tract. The balloons can be circumferentially wrapping around the inner and/or outer tubes. After the device reaches an initial position, balloon 4 is inflated to anchor the outer tube 3 on the bowel wall 2. The outer tube and its balloon are kept relatively stationary to the bowel wall part engaged by the inflated balloon, while the inner tube 5 moves forward to reach its distance. During the movement of the inner tube, an articulation mechanism such as the motor 14*a* and the base 14*b* shown in FIG. 2A may effect the articulation of a distal tip of the inner tube such that the inner tube may make turns following how the GI curves. Thus, the articulation mechanism may reduce or minimize stretching of the body cavity wall due to the movement of the inner tube. Both the inner and outer tubes, including the screw shown in the figure, may be made of flexible material. In addition, if relatively more rigid material is required, the outer tube including the screw may be made sufficiently small Once the inner tube 5 reaches a more distal destination, it is anchored on the bowel wall 2 by inflating the balloon 6. Then, the outer tube 3 follows by moving forward over the inner tube while the balloon 4 is deflated. FIG. 3 shows the balloon at the proximal end of the outer tube. However, it is to be understood that the balloon may be provided along the entire length of the outer tube. Similarly, it is not necessary that the balloon on the inner tube be at the very distal end; it may be provided along the length of the inner tube at a suitable position to permit the alternating extensions and retractions of the device. Once the outer tube is in place (more distal in the GI tract compared to the initial position), it is anchored on the bowel wall by inflating the balloon 4. The balloon 6 on the inner tube is then deflated and moves forward to an even more distal position. The process continues until it reaches a destination, such as a more distal desitantion in the GI tract, e.g., the small intestine.

Figure 4A:
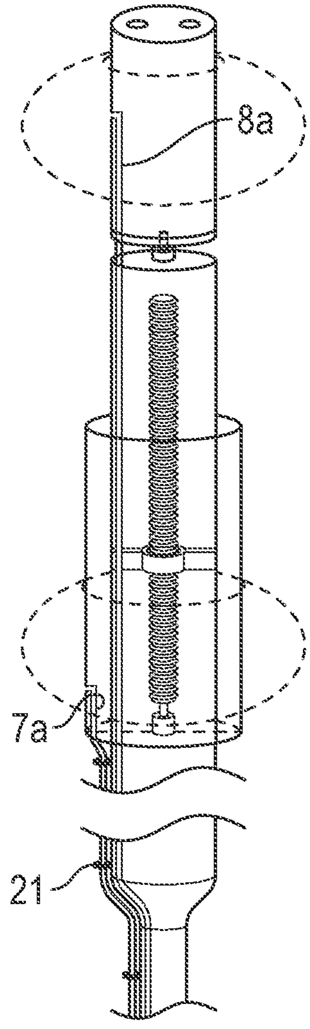
FIGS. 4A-4D show various exemplary configurations of the medium channels controlling the inflation and/or deflation of the balloons.
Figure 4B:
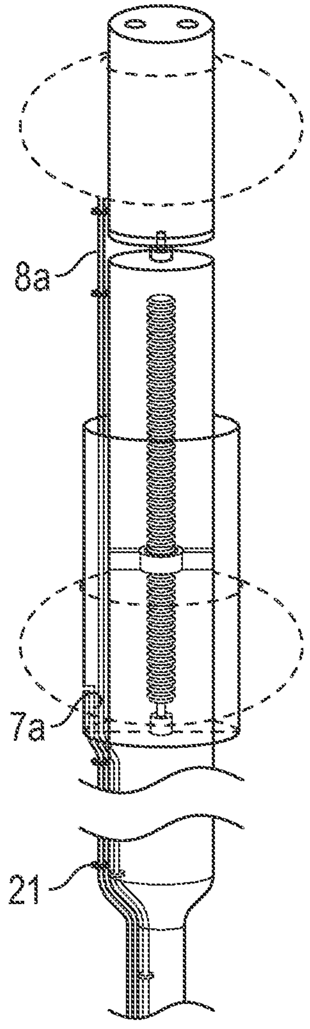
Figure 4C:
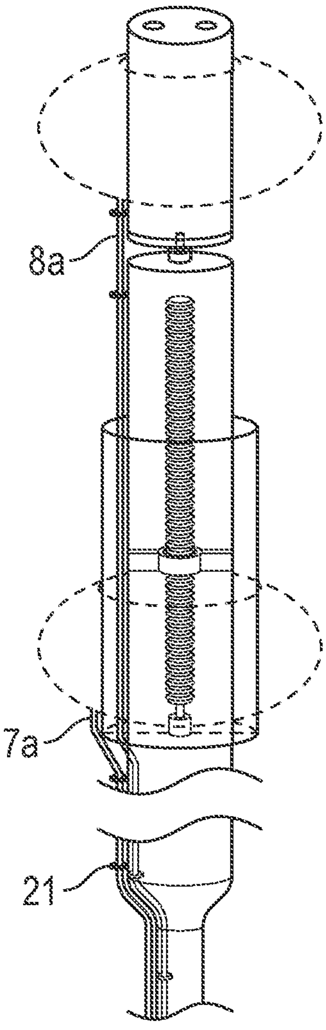
Figure 4D:
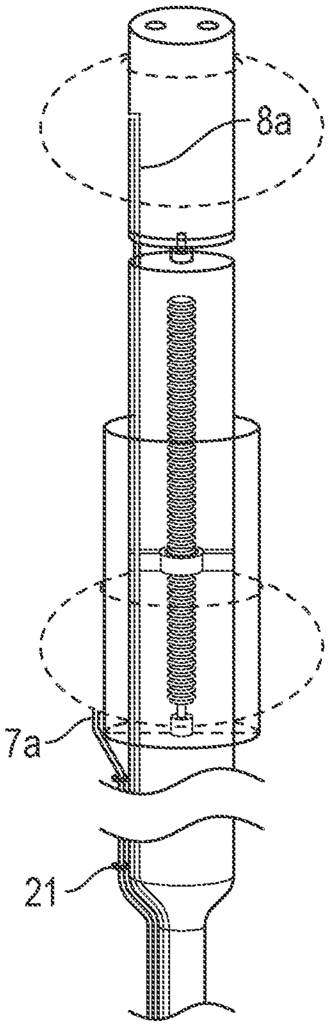

FIGS. 4A-4D show various configurations of the medium channels or tubing controlling the inflation and/or deflation of the balloons. FIG. 4A shows a medium channel or tubing 8*a* (connecting the balloon 6 to a medium source) inside the inner tube 5, and a medium channel or tubing 7*a* (connecting the balloon 4 to a medium source) inside the outer tube 3. FIG. 4B shows a medium channel or tubing 8*a* along the outside of the inner tube 5 and partially inside the outer tube 3, and a medium channel or tubing 7*a* inside the outer tube 3. FIG. 4C shows a medium channel or tubing 8*a* along the outside of the inner tube 5 and partially inside the outer tube 3, and a medium channel or tubing 7*a* along the outside of the outer tube 3. FIG. 4D shows a medium channel or tubing 8*a* inside the inner tube 5, and a medium channel or tubing 7*a* along the outside of the outer tube 3. The medium channel or tubing may be tethered to the outer or inner tube by tethering mechanisms 21.

Figure 7:
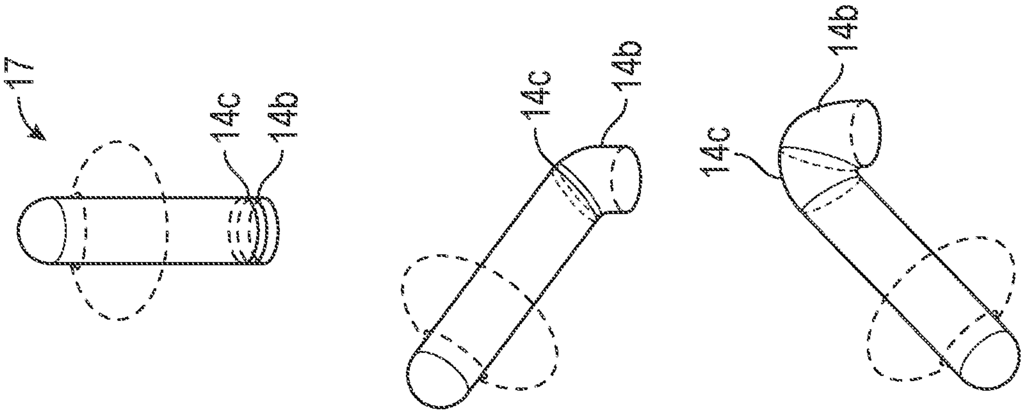
FIG. 7 shows exemplary mechanisms involving an additional chamber on top of the base to effect articulation of the distal end portion of the inner tube.
Figure 6:
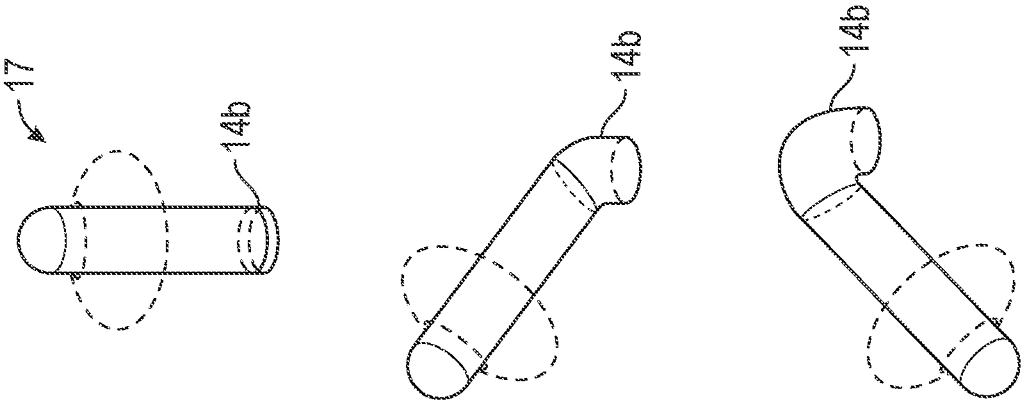
FIG. 6 shows exemplary mechanisms for a chamber in the base of the tip portion of the inner tube to effect articulation of the distal end portion of the inner tube.
Figure 5:
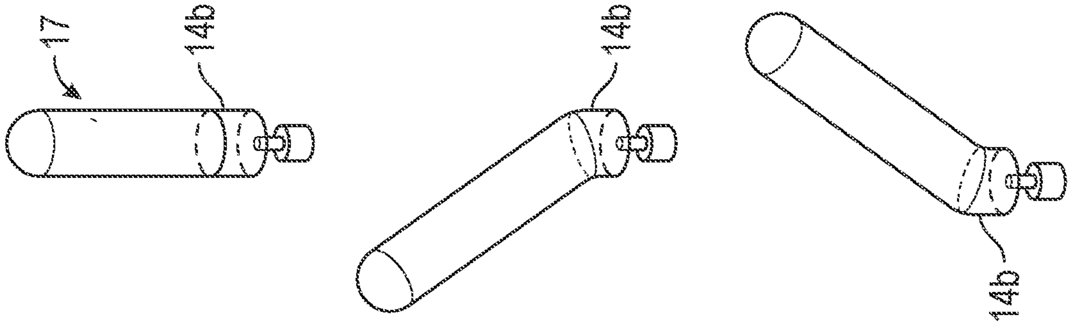
FIG. 5 shows exemplary mechanisms for the rotation and tilting of the tip portion of the inner tube, in order to guide the inner tube to move in various directions, e.g., following the curves of the body cavity.

FIG. 5 shows by combining rotation of the base 14*b* and tilting the tip 17, the tip portion of the inner tube is capable of guiding the inner tube to move in various directions. The base 14*b* is a flexible conduit-like structure, except it is asymmetrical and has a hinge at one side. As shown in FIG. 6, the chamber of the round base 14*b* can maintain an angle from 0 degree to 180 degree at the hinge by inflating the base chamber, in order to effect articulation of the distal end portion 17 of the inner tube. Another chamber 14*c* can be provided on top of the base 14*b* to share the same hinge with the base, as shown in FIG. 7.

Figure 10:
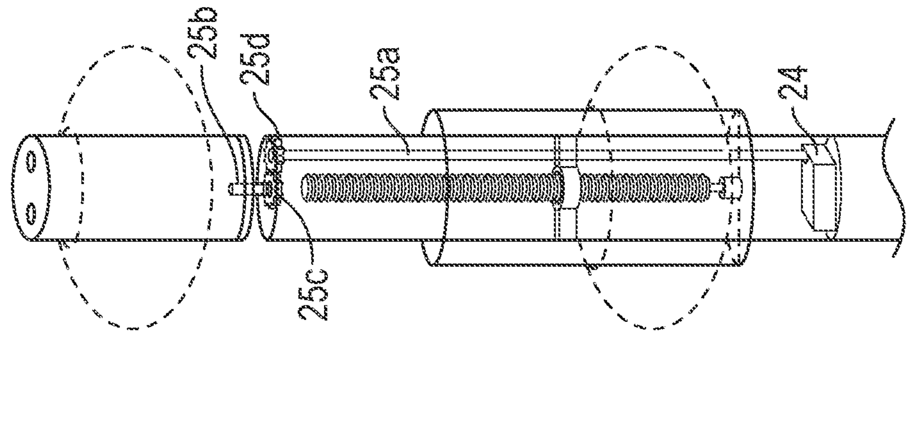
FIG. 10 shows an exemplary mechanism involving the rotation of a servo motor placed proximal to the first stepper motor for the screw/nut, in order for the rotation be to transmitted to the base to effect articulation.
Figure 9:
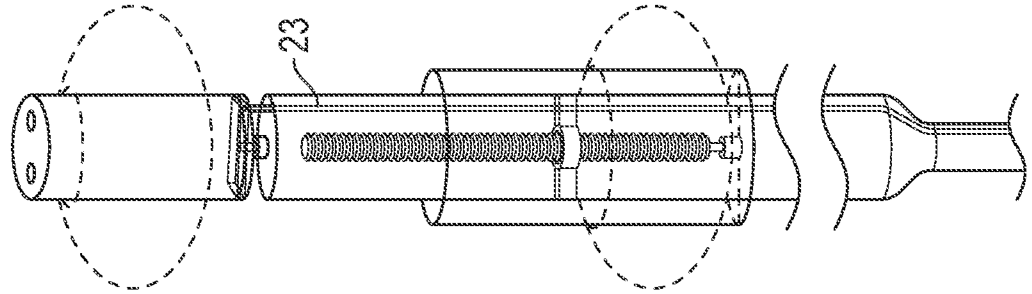
FIG. 9 shows an exemplary air channel going through the inner tube body and connecting to the base.
Figure 8:
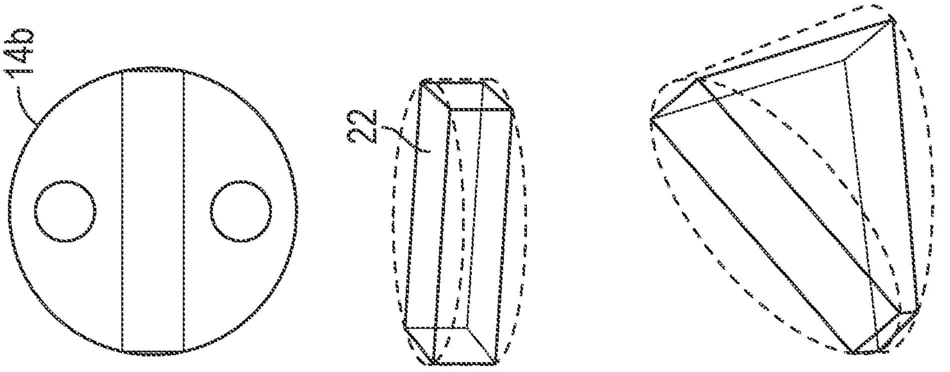
FIG. 8 shows an exemplary chamber within the base.

FIG. 8 shows inside the round base 14*b*, there is a thin cuboid shaped chamber 22 that can be inflated asymmetrically to a triangular shape, thereby inflating the round base to a desired angle. FIG. 9 shows a medium channel or tubing 23 (e.g., the medium can be a gas, a liquid, or a mixture thereof such as a vapor) going through the inner tube body and connect to the round base via a flexible conduit. FIG. 10 shows a servo motor 24 can be placed proximal to the first stepper motor 13 for the screw/nut and connected to the round base with a stiff thin wire 25*a* that can accurately transmit the servo motor's rotation to a pin 25*b* on the round base via gears 25*c* and 25*d*.

Figure 11:
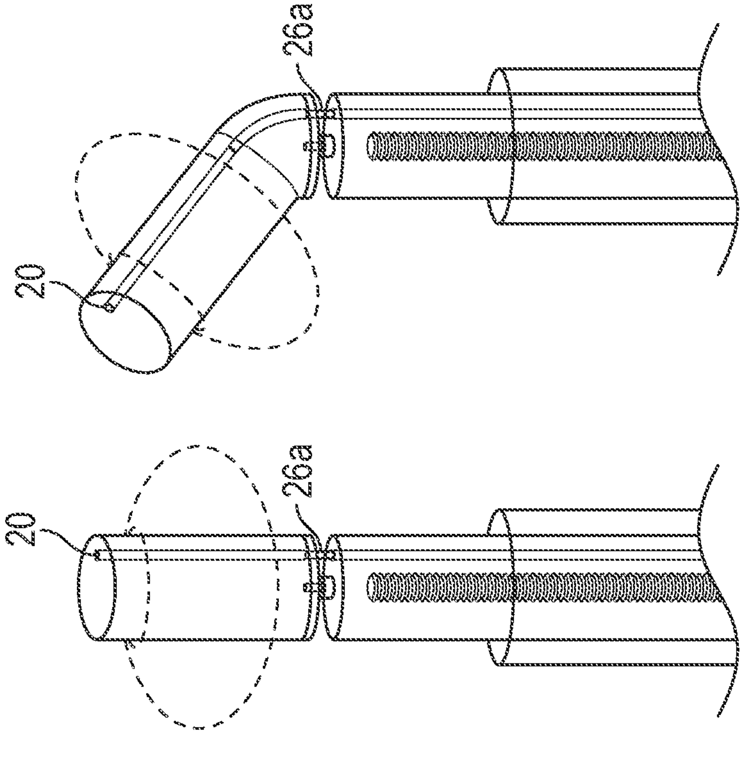
FIG. 11 shows an exemplary water/air/suction channel traversing the inner tube.
Figure 12:
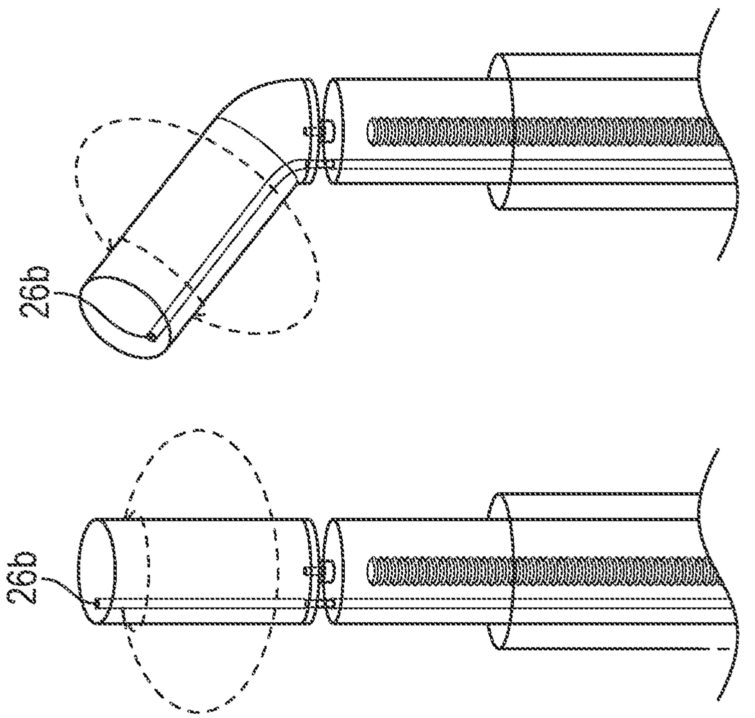
FIG. 12 shows an exemplary optical fiber or wire of a camera traversing the inner tube.
Figure 13:
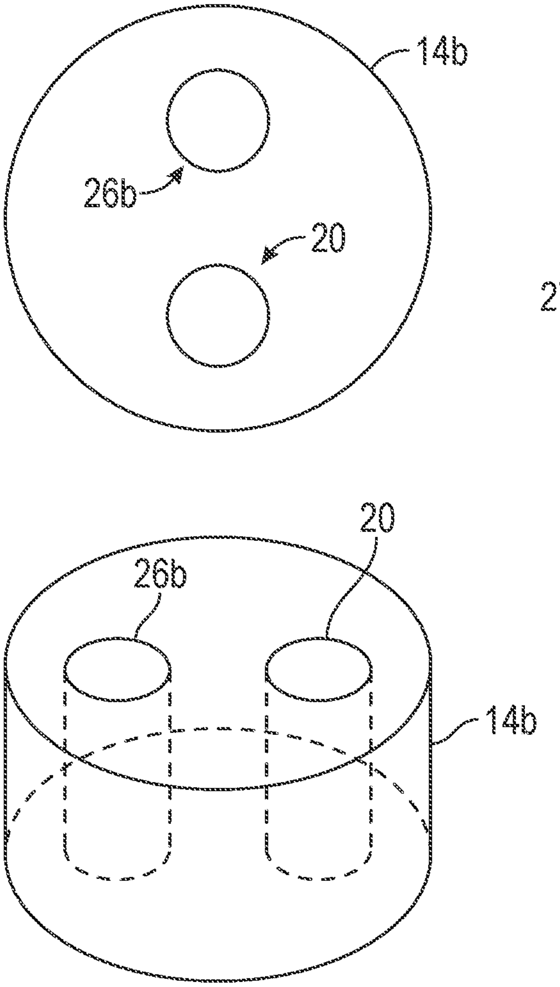
FIG. 13 shows an exemplary camera channel and an exemplary water/air/suction channel passing the round base through an air-sealed tunnel.

FIG. 11 shows the water/air/suction channel 20 is a channel traversing the whole inner tube from the proximal inner tube, round base to the distal inner tube. There is a flexible tube 26*a* that is fixed to the proximal end of the channel at the distal (tip) section of the inner tube and end freely in the air channel of the inner tube body but fits tightly in the air channel of the inner tube body to maintain a seal. The flexible tube traverses the round base down to the inner tube body at a length that is long enough to still remain in the tube body's air channel when the round base is inflated to its largest angle at the hinge and when the round base rotates up to 180 degree to both directions (clockwise and counter-clockwise). FIG. 12 shows the optical fiber or wire of a camera can traverse the entire inner tube and/or traverse the round base. FIG. 13 shows the camera channel 26*b* and water/air/suction channel 20 pass the base 14*b* through an air-sealed tunnel to ensure that the base is air sealed.

Figure 14:
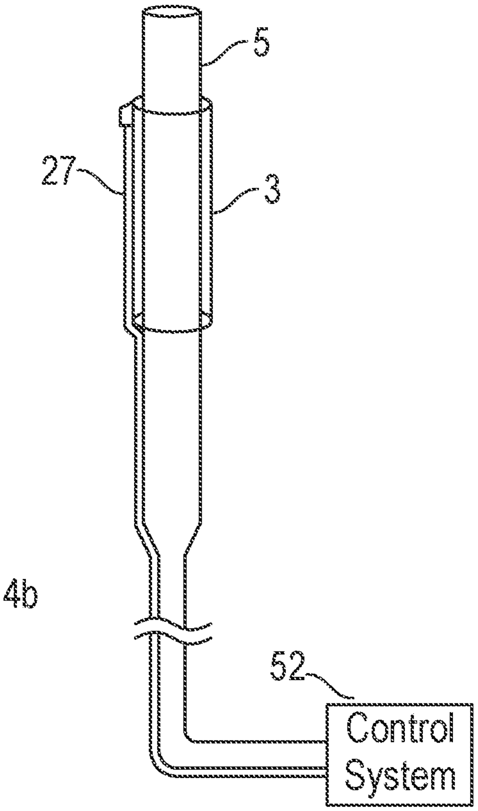
FIG. 14 shows an exemplary guidewire attached to the outer tube and the inner tube.

FIG. 14 shows a guidewire 27 attached to the outer tube distally and to the inner tube proximally, for example, as a carrier system that allows other mechanisms to feed over the guidewire and be delivered to a desired location. The device may further comprise the control unit or system 52.

Figure 15A:
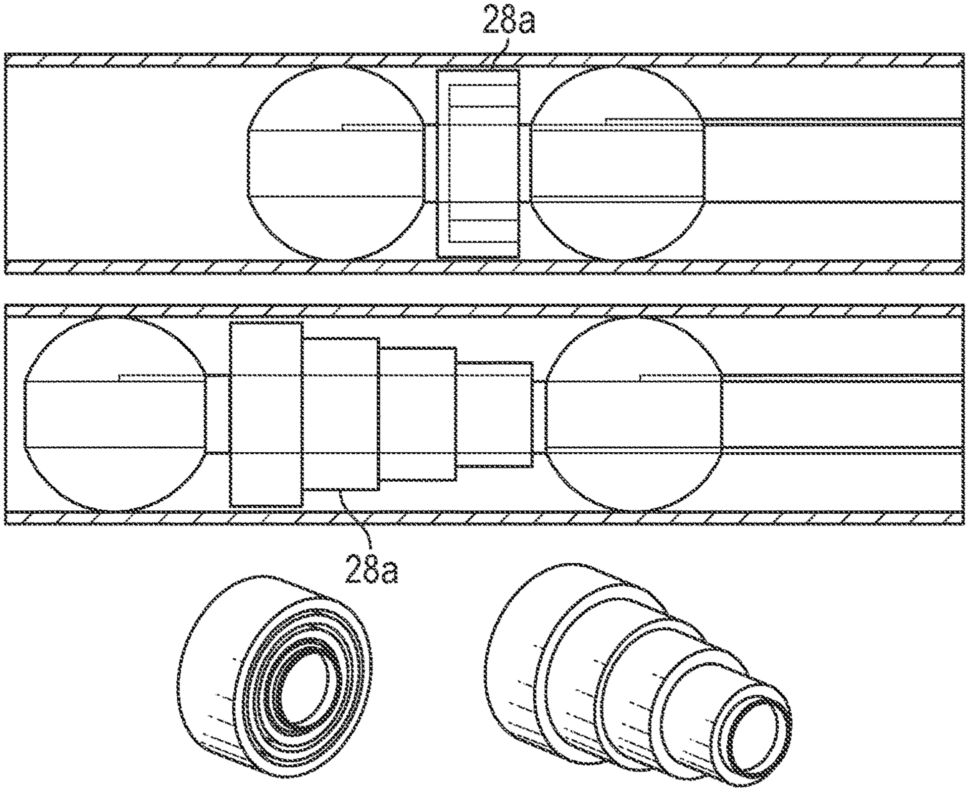
FIG. 15A shows an exemplary actuating mechanism comprising a controllably expandable telescoping structure to effect longitudinal movement of the device.

The device may be driven by an actuating mechanism based on one or more controllably expandable telescoping structure. FIG. 15A shows an actuating mechanism comprising a controllably expandable telescoping structure 28*a*, to effect alternating extensions and retractions of a distance between the balloons 4 and 6. A controllably expandable telescoping structure may comprise a plurality of coaxial cylindrical sections which when inflated are slidable within one another. Methods of making telescoping or nested balloons are known, for example, as shown in US 2016/0114141, which is incorporated by reference in its entirety. The controllably expandable telescoping structure may comprises one or more telescoping balloons, which are collapsed or nested when no or little pressure is applied inside the balloons and expand when pressure is applied. Thus, the controllably expandable telescoping structure may be use to provide a worm-like or caterpillar type action to advance the distal portion of the device in a body passageway. By use of the telescoping structure which have a very minor length dimension compared to a traditional endoscope, tight curves in a body passageway can be easily maneuvered around.

Figure 15B:
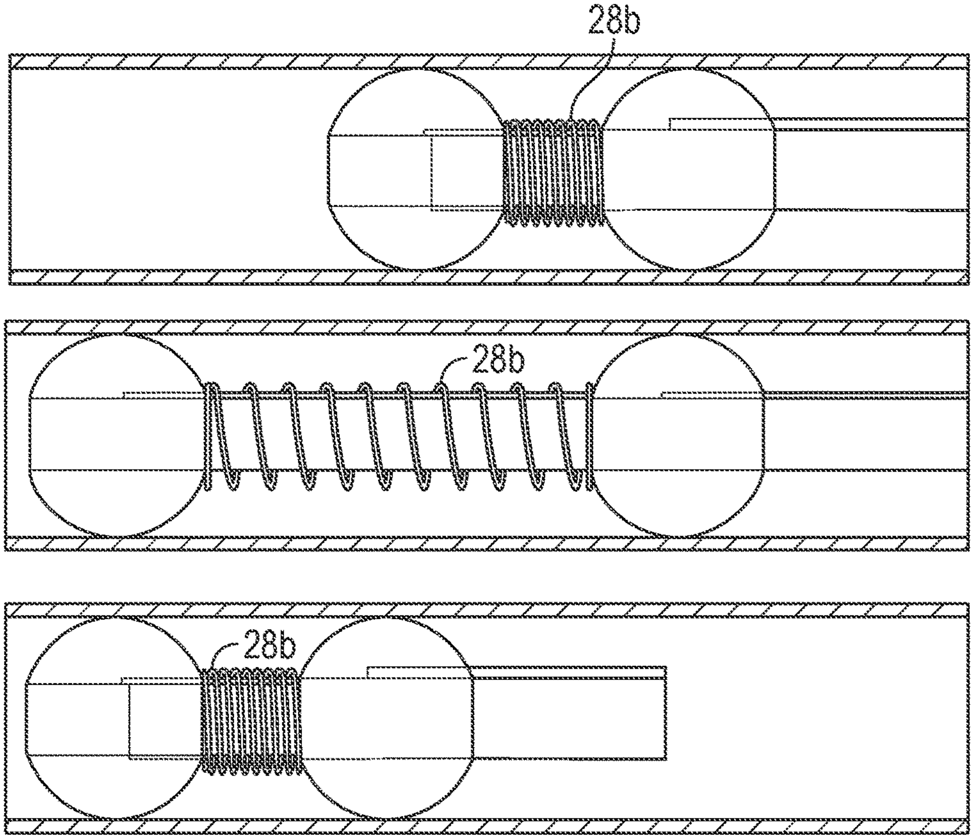
FIG. 15B shows an exemplary shape memory alloy actuating mechanism to effect longitudinal movement of the device.

The device may also be driven by a shape memory alloy-based actuating mechanism. FIG. 15B shows a shape memory alloy actuating mechanism 28*b* to effect alternating extensions and retractions of a distance between the balloons 4 and 6. The shape memory alloy actuating mechanism may comprises one or more shape memory alloy spring. The shape memory alloy has a first, relaxed state or phase (e.g, when no power is provided) and a second, actuated state or phase (e.g., when a voltage is provided). When power is withdrawn, the shape memory alloy returns to its relaxed state or phase. When shaped into a spring, the transition of the shape memory alloy from the relaxed state to the actuated state causes linear motion along the axis of the spring that is applied to the mechanical interface coupling the inner tube and the outer tube. Because of its narrow profile and linear orientation, the shape memory alloy actuating mechanism may be use to provide a worm-like or caterpillar type action to advance the distal portion of the device in a body passageway.

Figure 15C:
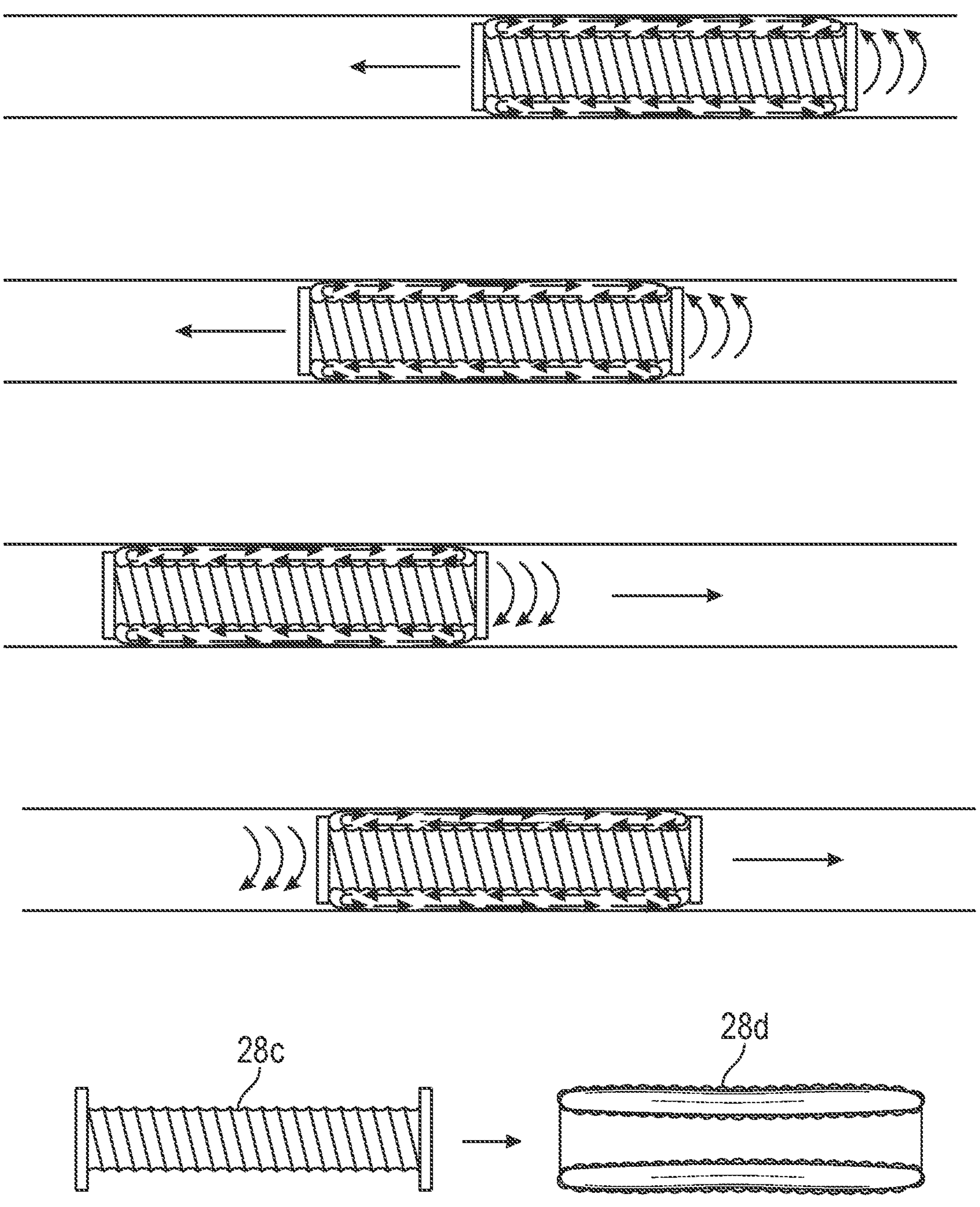
FIG. 15C shows an exemplary mechanism to effect longitudinal movement of the device.

The device may also be driven by a snake traction mechanism, such as a snake traction sleeve shown in FIG. 15C. A rotating tube 28*c* with threads molded into it may push the inside of the traction sleeve 28*d* in one direction to get motion of the assembly in the opposite direction. In some embodiments, a snake traction sleeve may be provided between an inner member and an outer member to effect the sliding movement between the outer member and the inner member.

Figure 16:
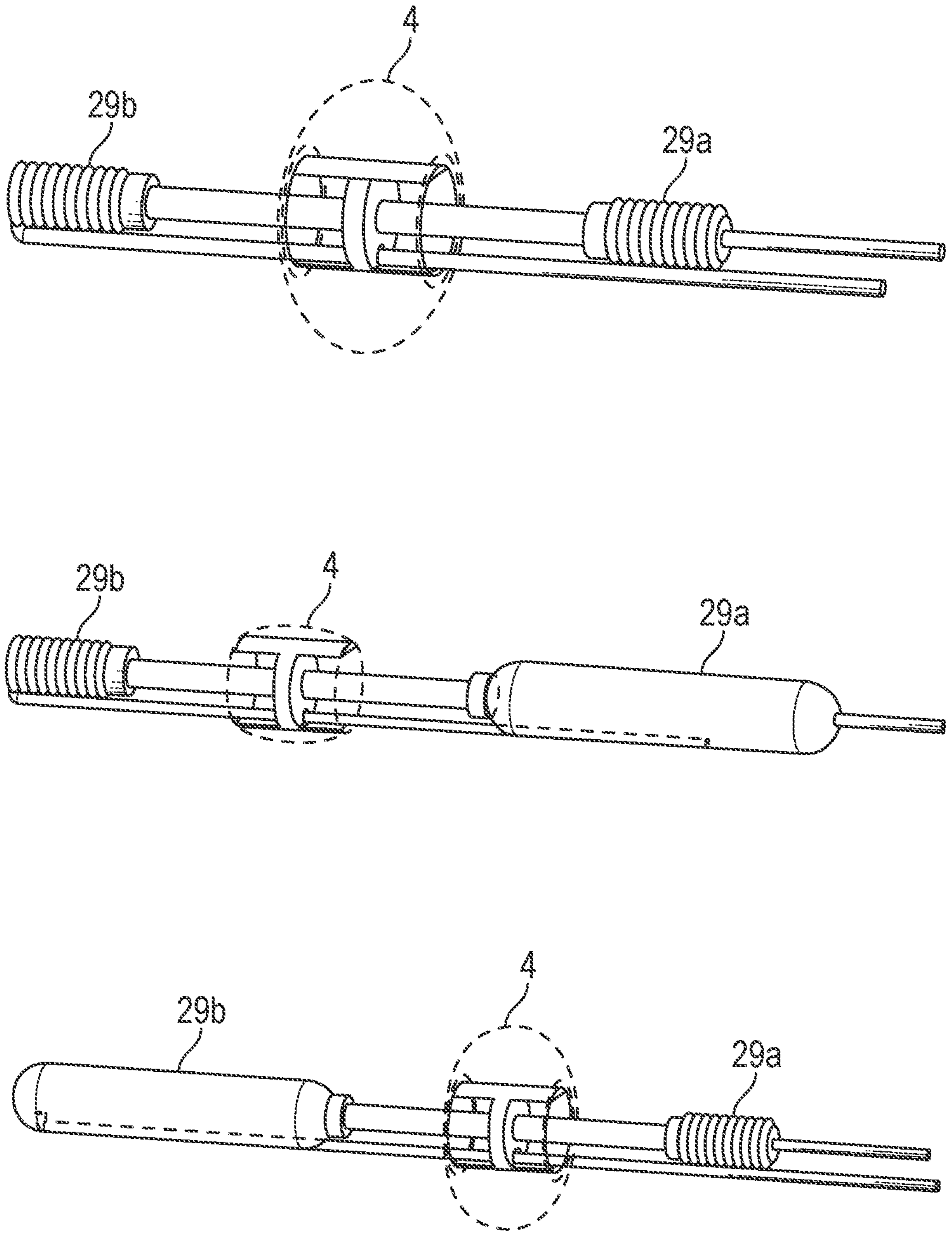
FIG. 16 shows exemplary controllably expandable structures configured to expand or contract longitudinally, thereby effecting longitudinal movement of the device.

FIG. 16 shows controllably expandable structures configured to expand or contract longitudinally, thereby effecting the sliding movement between the outer member 3 (and its balloon 4) and the inner member (not shown). The controllably expandable structures may comprise one or more compliant balloons 29*a* and 29*b*. Compliant balloon 29*a* is proximal to the balloon 4 while compliant balloons 29*b* is distal to the balloon. Compliant balloons 29*a* and 29*b* are each connected to a medium source via a channel to controllably expand or contract the balloons. As shown in FIG. 16, upper panel, when balloon 4 is expanded and engage a body cavity wall (not shown), both compliant balloons 29*a* and 29*b* are deflated and the folds of the balloons are collapsed. FIG. 16, middle panel, shows when balloon 4 is deflated (while balloon 6 is inflated to anchor onto a body cavity wall), the proximal compliant balloon 29*a* may be expanded, and its longitudinal expansion drives or propels the outer member 3 (and its balloon 4) to a more distal position within the body cavity. FIG. 16, lower panel, shows balloon 4 is again inflated and outer member 3 is held stationary (while balloon 6 is deflated such that the inner member can move), the distal compliant balloon 29*b* may be expanded in the longitudinal direction to further drive the inner member 3 (and its balloon 4) to a more distal position within the body cavity.

Figure 17A:
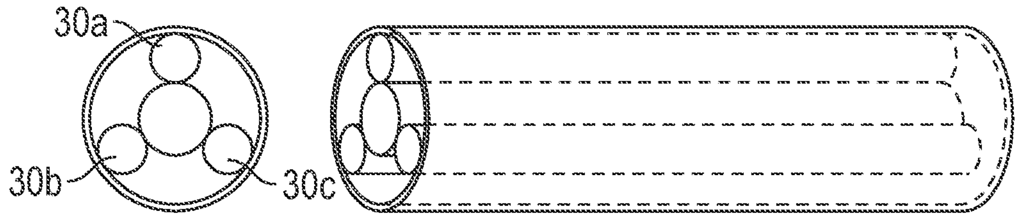
FIG. 17A-17D show exemplary controllably expandable structures configured to expand or contract, thereby effecting longitudinal movement of the device and/or articulation of the device, e.g., articulation of the distal portion of the inner tube in a direction transverse to the longitudinal axis of the body portion of the inner tube.
Figure 17B:
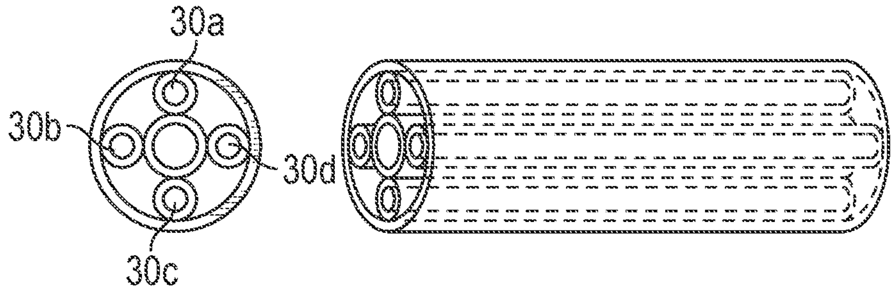
Figure 17C:
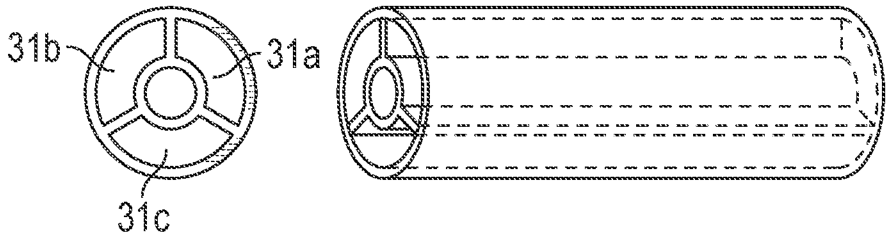
Figure 17D:
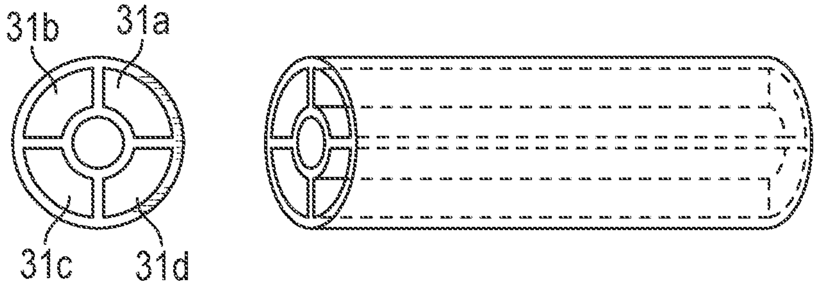

FIGS. 17A-17D show controllably expandable structures configured to expand or contract, thereby effecting the sliding movement between the outer member and the inner member and/or effecting articulation of the distal portion in a direction transverse to the longitudinal axis of the body portion of the inner tube. FIG. 17A shows the controllably expandable structures may comprise three pressure balloons 30*a,* 30*b,* and 30*c,* e.g., as motor balloons (e.g., for driving longitudinal movement) and/or steering balloons (e.g., for articulation of the distal tip). One or more of the pressure balloons may be selectively expanded and/or expanded to different degrees (e.g., by using different inflation pressures) such that the distal tip of the inner tube may be turned in a desired direction. FIG. 17B shows the controllably expandable structures may comprise four pressure balloons 30*a,* 30*b,* 30*c,* and 30*d,* e.g., as motor balloons (e.g., for driving longitudinal movement) and/or steering balloons (e.g., for articulation of the distal tip). FIG. 17C shows the controllably expandable structures may comprise three pressure chambers 31*a,* 31*b,* and 31*c,* e.g., as motor chambers (e.g., for driving longitudinal movement) and/or steering chambers (e.g., for articulation of the distal tip). One or more of the pressure chambers may be selectively expanded and/or expanded to different degrees (e.g., by using different inflation pressures) such that the distal tip of the inner tube may be turned in a desired direction. FIG. 17D shows the controllably expandable structures may comprise four pressure chambers 31*a,* 31*b,* 31*c,* and 31*d,* e.g., as motor chambers and/or steering chambers. It is to be understood that in any of the preceding embodiments, the controllably expandable structures can be bellows (e.g., as shown in FIG. 20A) instead of pressure balloons or pressure chambers, and the bellows can be assembled from a plurality of unit bellows (e.g., as shown in FIGS. 23A-23H).

Figure 18:
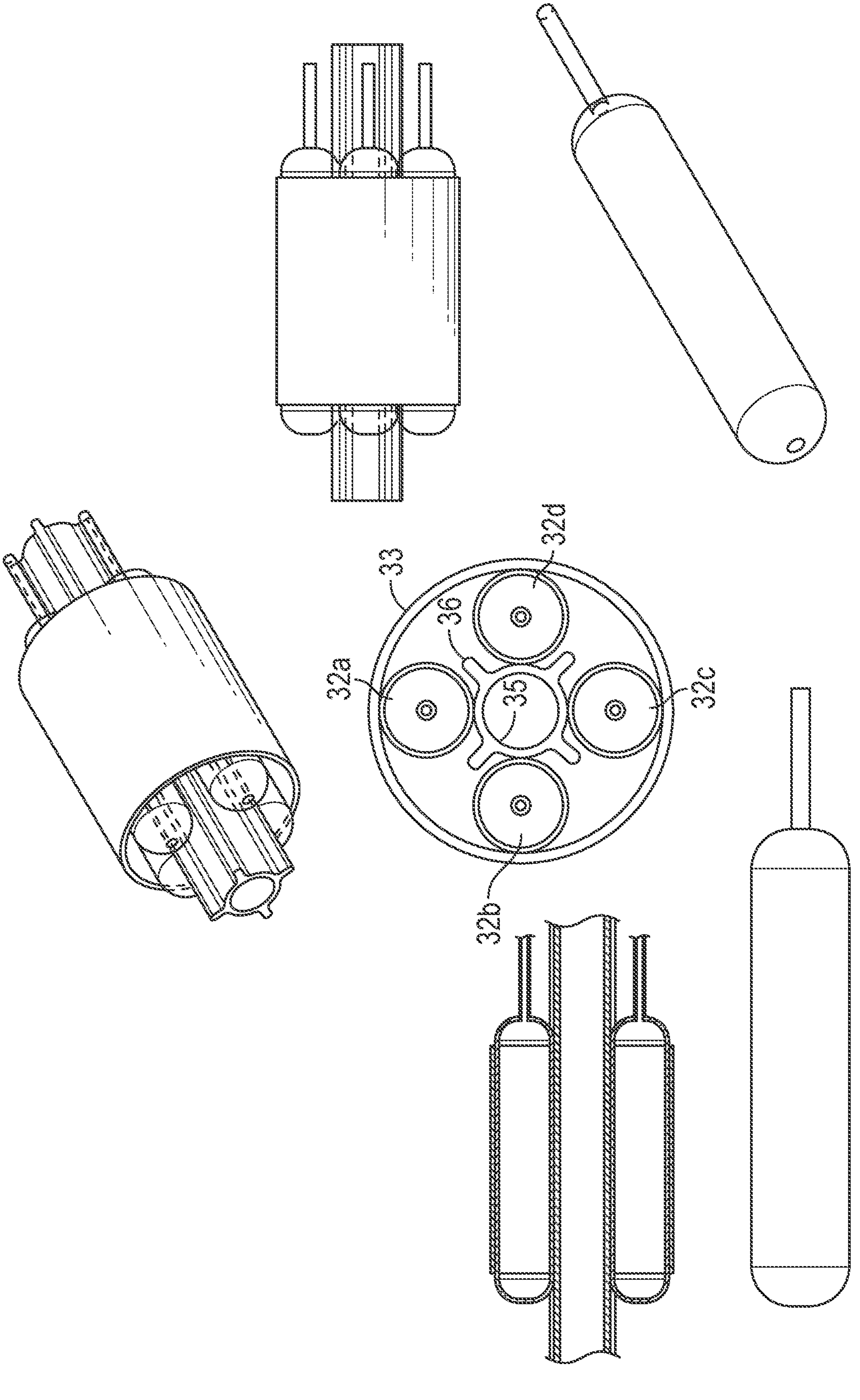
FIG. 18 shows four exemplary pressure balloons configured to expand or contract, thereby effecting longitudinal movement of the device and/or articulation of the device, e.g., articulation of the distal portion of the inner tube in a direction transverse to the longitudinal axis of the body portion of the inner tube.

FIG. 18 shows four pressure balloons 32*a,* 32*b,* 32*c,* and 32*d,* configured to expand or contract, thereby effecting the sliding movement between the outer member 33 and the inner member 35 and/or effecting articulation of the distal portion of the inner member in a direction transverse to the longitudinal axis of the body portion of the inner member. Each of four pressure balloons may be connected to a medium channel 34 for controllably expanding one or more of the pressure balloons. The pressure balloons may be separated by ridges 36 which may serve as dividers. It is to be understood that in any of the preceding embodiments, the controllably expandable structures can be bellows (e.g., as shown in FIG. 20A) instead of pressure balloons or pressure chambers, and the bellows can be assembled from a plurality of unit bellows (e.g., as shown in FIGS. 23A-23H).

In some embodiments, the multiple balloon/bellows/channel design (e.g., as shown in FIGS. 17A-17D) and/or the unit bellows design (e.g., as shown in FIGS. 23A-23H) may be used to allow and/or control the rotation or articulation of a distal tip of the device disclosed herein, e.g., the distal portion of the inner tube. In some embodiments, the distal portion of the inner tube can form an angle from 0 degree to 180 degree relative to a body portion of the device such as a body portion of the inner tube. For example, the angle between the distal portion of the inner tube and the body portion of the device can be about 30 degrees, about 45 degrees, about 60 degrees, about 75 degrees, about 90 degrees, about 105 degrees, about 120 degrees, about 135 degrees, about 150 degrees, about 165 degrees, or about 180 degrees.

Figure 19:
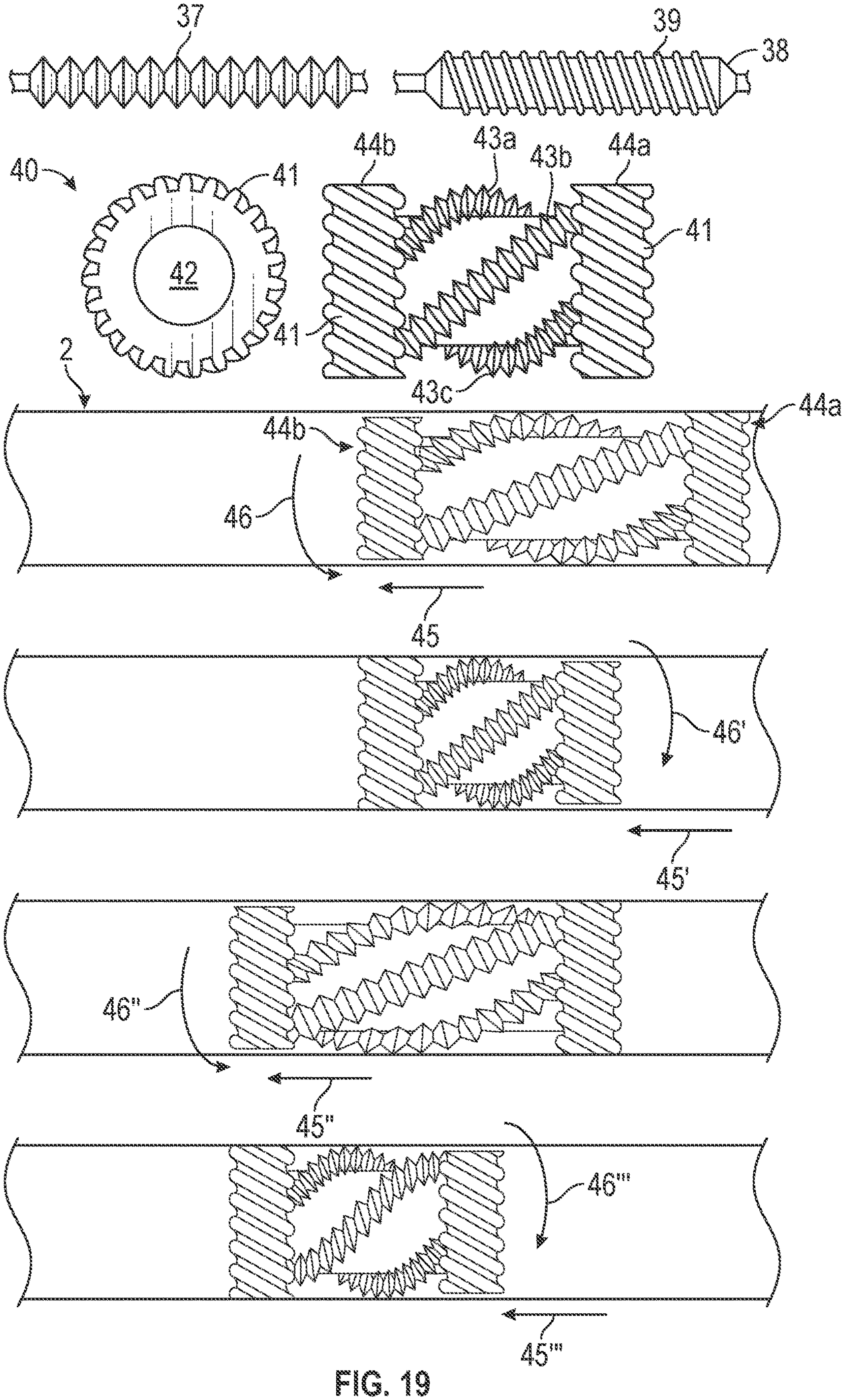
FIG. 19 shows an exemplary helical mechanism to effect longitudinal movement of the device and/or articulation of the device, e.g., articulation of the distal portion of the inner tube in a direction transverse to the longitudinal axis of the body portion of the inner tube.

The sliding movement between the outer member 33 and the inner member 35 may also be actuated or driven by one or more controllably expandable structures, such as one or more bellows 37, one or more balloons 38 in combination with one or more springs 39 (e.g., a spring spiraling or wrapping around a balloon), as shown in FIG. 19, or any suitable combination thereof. The bellows may be compliant, such as a compliant ridge bellows. The bellows may be axially compliant and have a length that exhibits uniform axial expansion during inflation of the bellows, while being radially non-compliant in that the bellows do not expand or substantially do not expand radially during inflation. Similarly, the balloons may be compliant, such as axially compliant, and have a length that exhibits uniform axial expansion during inflation while being radially non-compliant in that the radius of each balloon exhibits little or no radial growth during inflation of the balloon. Alternatively, a balloon may be compliant but because of the spring around it, the balloon does not expand or substantially do not expand radially during inflation but is able to axially expand together with the axially expanding spring.

The one or more controllably expandable elements, such as the first and second balloons for engaging the wall of a body cavity, may comprise a tire-like or helical gear-like structure 40 having treads 41 on an outer surface. The tire-like or helical gear-like structure may have a through hole 42 having an inner surface for engaging the inner member or the outer member. The first and second balloons having treads (e.g., diagonal treads) may function as traction balloons, and may be connected to each other by one or more controllably expandable structures, such as a plurality of controllably expandable structures forming a helix. As shown in FIG. 19, three controllably expandable structures 43*a*, 43*b*, and 43*c* may connect the first and second traction balloons 44*a* and 44*b* and form a three-member helix. The controllably expandable structures may connect the outer member and the inner member at suitable structures other than the first and second balloons, respectively, thus indirectly connecting the first and second balloons.

The first and second traction balloons 44*a* and 44*b* facilitate fixing the outer and inner members, respectively, to the body cavity wall 2 when the balloons are radially expanded. For example, traction balloon 44*a* may be radially expanded, and with the treads providing more traction, securely press against the body cavity wall, thereby fixing the outer member (not shown in FIG. 9) to the body cavity wall. The controllably expandable structures 43*a*, 43*b*, and 43*c* may be inflated while traction balloon 44*b* is deflated or not fully inflated (e.g., inflated but not to the extent that it may be fixed onto body cavity wall during movement). Inflation of the helical drives increases the lengths of the controllably expandable structures 43*a*, 43*b*, and 43*c*, thereby effecting axial movement 45 of traction balloon 44*b*, e.g., toward a more distal portion of the body cavity. Inflation of the helical drives also causes twisting/untwisting of the controllably expandable structures 43*a*, 43*b*, and 43*c*, thereby effecting rotational movement 46 of traction balloon 44*b*. When traction balloon 44*b* reaches its destination, it may be radially expanded, and with the treads providing more traction, securely press against a more distal body cavity wall, thereby fixing the inner member (not shown in FIG. 9) to the more distal body cavity wall. At this time, traction balloon 44*a* may be radially deflated, thereby releasing it from secure attachment to the body cavity wall and allowing axial movement 45' of the outer member along the body cavity. During the deflation, controllably expandable structures 43*a*, 43*b*, and 43*c* become shorter in lengths to bring traction balloon 44*a* (and the outer member connected thereto) closer to the fixed traction balloon 44*b*. Twisting/untwisting of controllably expandable structures 43*a*, 43*b*, and 43*c* during the deflation also causes rotational movement 46' of traction balloon 44*a*. When traction balloon 44*a* reaches a more distal position, it may be radially expanded again to securely press against the body cavity wall, while traction balloon 44*b* is deflated or not fully inflated (e.g., inflated but not to the extent that it may be fixed onto body cavity wall during movement). Controllably expandable structures 43*a*, 43*b*, and 43*c* are inflated, effecting axial movement 45'' and rotational movement 46'' of traction balloon 44*b*. When traction balloon 44*b* reaches an even more distal position, it may be radially expanded to securely press against an even more distal body cavity wall. At this time, traction balloon 44*a* is radially deflated, effecting axial movement 45''' and rotational movement 46''' of traction balloon 44*a* and bringing it closer to the fixed traction balloon 44*b*. The process steps may be repeated to place the device in a desired position in the body cavity, such as in the small intestine.

In any of the preceding embodiments, one or more of the controllably expandable structures, such as helical drives 43*a*, 43*b*, and 43*c*, may be selectively and/or preferentially inflated and/or deflated. For example, one or more of the controllably expandable structures may be inflated, while the remaining controllably expandable structure(s) is/are deflated, not inflated, or inflated to a greater or lesser degree. Alternatively, one or more of the controllably expandable structures may be deflated, while the remaining controllably expandable structure(s) is/are inflated, not deflated, or deflated to a greater or lesser degree. A suitable combination of the inflation/deflation statuses of the plurality of controllably expandable structures may be used to effect controllable and/or precise articulation of the inner member and/or the outer member, such as a distal portion of the inner member (e.g., the inner tube), thereby allowing the device to follow the curves of the body cavity during the movement. In some aspects, the controllable articulation avoids or reduces stretching of the body cavity wall, thereby avoiding or reducing discomfort during the procedure.

Figure 20C:
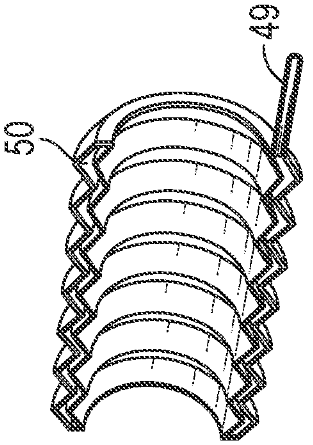
FIG. 20A-20F show exemplary bellows designs, which may be used to effect longitudinal movement of the device and/or articulation of the device, e.g., articulation of the distal portion of the inner tube in a direction transverse to the longitudinal axis of the body portion of the inner tube.
Figure 20B:
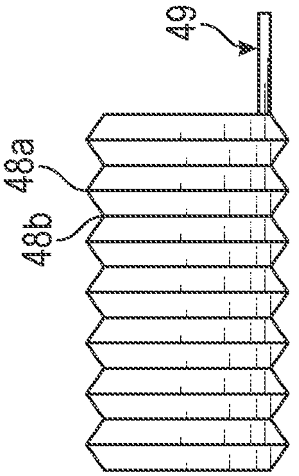
Figure 20A:
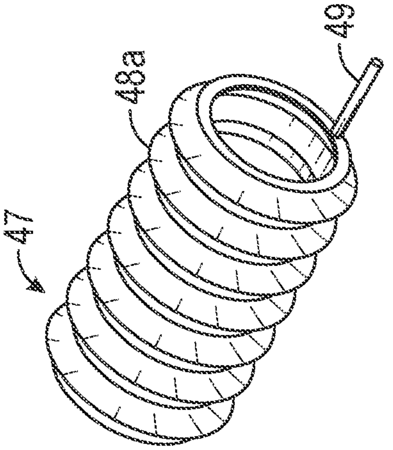
Figure 20F:
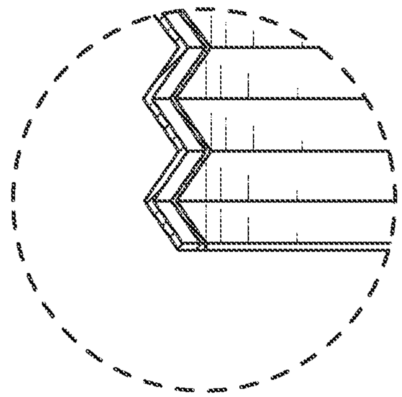
Figure 20E:
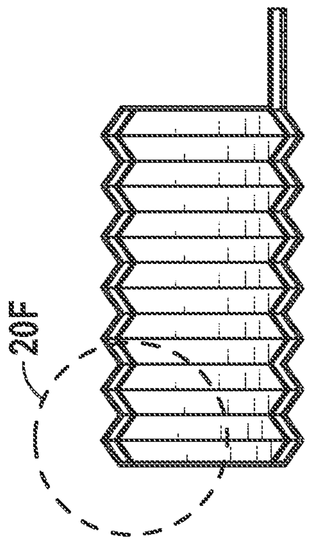
Figure 20D:
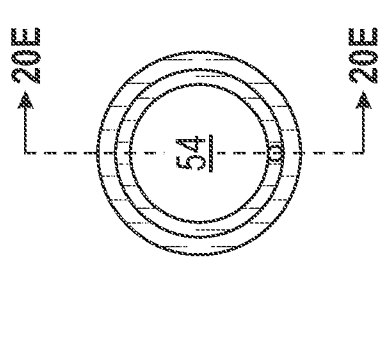

The one or more controllably expandable structures may comprise ridge bellows, for example, as shown in FIGS. 20A-20F. As shown in FIG. 20A (prosective view) and FIG. 20B (side view) and, bellows 47 may be an axially expandable bellows comprising a plurality of folds each having a ridge 48*a* and a valley 48*b*. The bellows may comprise an outer layer (having an outer surface and an inner surface) and an inner layer (having an outer surface and an inner surface), and the inner surface of the outer layer and the outer surface of the inner layer may sandwich a medium space 50, for example, for a gas, a liquid, or a combination thereof (e.g., a vapor). A medium may be provided to and/or withdrawn from medium space 50 through an inlet/outlet 49, in order to controllably expand and/or contract bellows 47. FIG. 20C shows a view of the bellows cut in half along the axis. The bellows may also have an internal hollow 54 that may be used to housing one or more tubing, channel, and/or wire such as electric wire. The bellows may be connected to the inner member or the outer member. For example, the bellows may house at least a portion of the inner member or the outer member in its hollow and engage the inner member or the outer member through the inner surface of the bellow's inner layer. Thus, the bellows may act as or as part of an actuating mechanism to effect the relative sliding movement between the inner and outer members. FIG. 20D shows a cross sectional view of the bellows. FIG. 20E shows the bellows cut in half along the axis, and an expanded view is provided in FIG. 20F.

Figure 21:
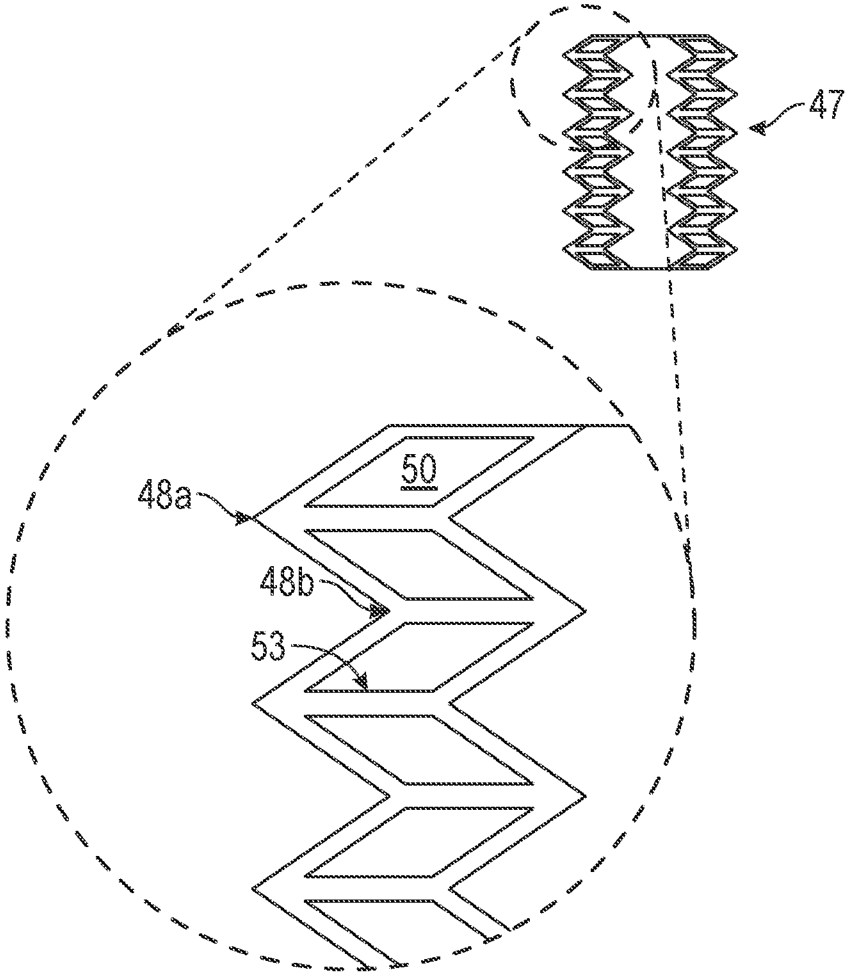
FIG. 21 and FIG. 22 show exemplary bellows designs comprising one or more supporting structures.
Figure 22:
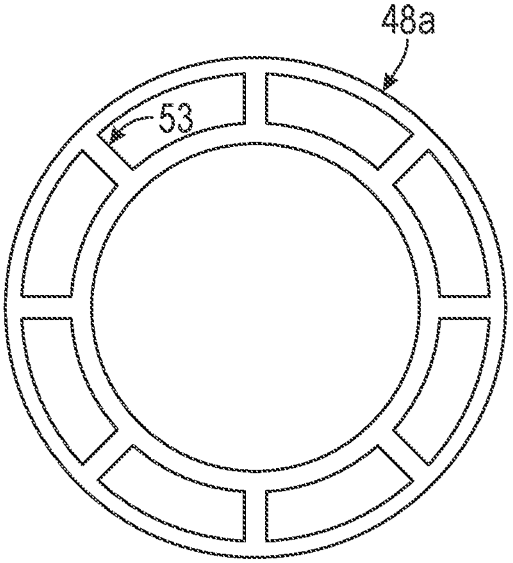

The bellows may comprise internal supports, such as one or more spokes or struts, in the medium space. The internal supports may be molded into the parts (e.g., inner and outer layers) of the bellows so that the parts stay uniform when pressurized. As shown in FIG. 21, a cross sectional view of the bellows shows ridge 48*a*, valley 48*b*, medium space 50 (such as an air or gas space), and spokes 53 connecting the outer layer and the inner layer of the bellows. Although FIG. 21 shows medium space 50 is separated into a plurality of spaces, it should be understood that the plurality of spaces are configured to be gas, liquid, or fluid communication with each other forming the medium space 50, and spokes 53 do not physically isolate the plurality of spaces. For example, a spoke may be provided between a ridge of the outer layer and the corresponding ridge of the inner layer, and/or a valley of the outer layer and the corresponding valley of the inner layer. As shown in FIG. 22, a cross sectional view, spokes 53 may serve to support the inner and outer layers or walls of the bellows relative to each other, so that the envelope of the bellows remains within a designed size when pressurized.

Figures 23A, 23B, 23C, 23D, 23E, 23F, 23G, 23H:
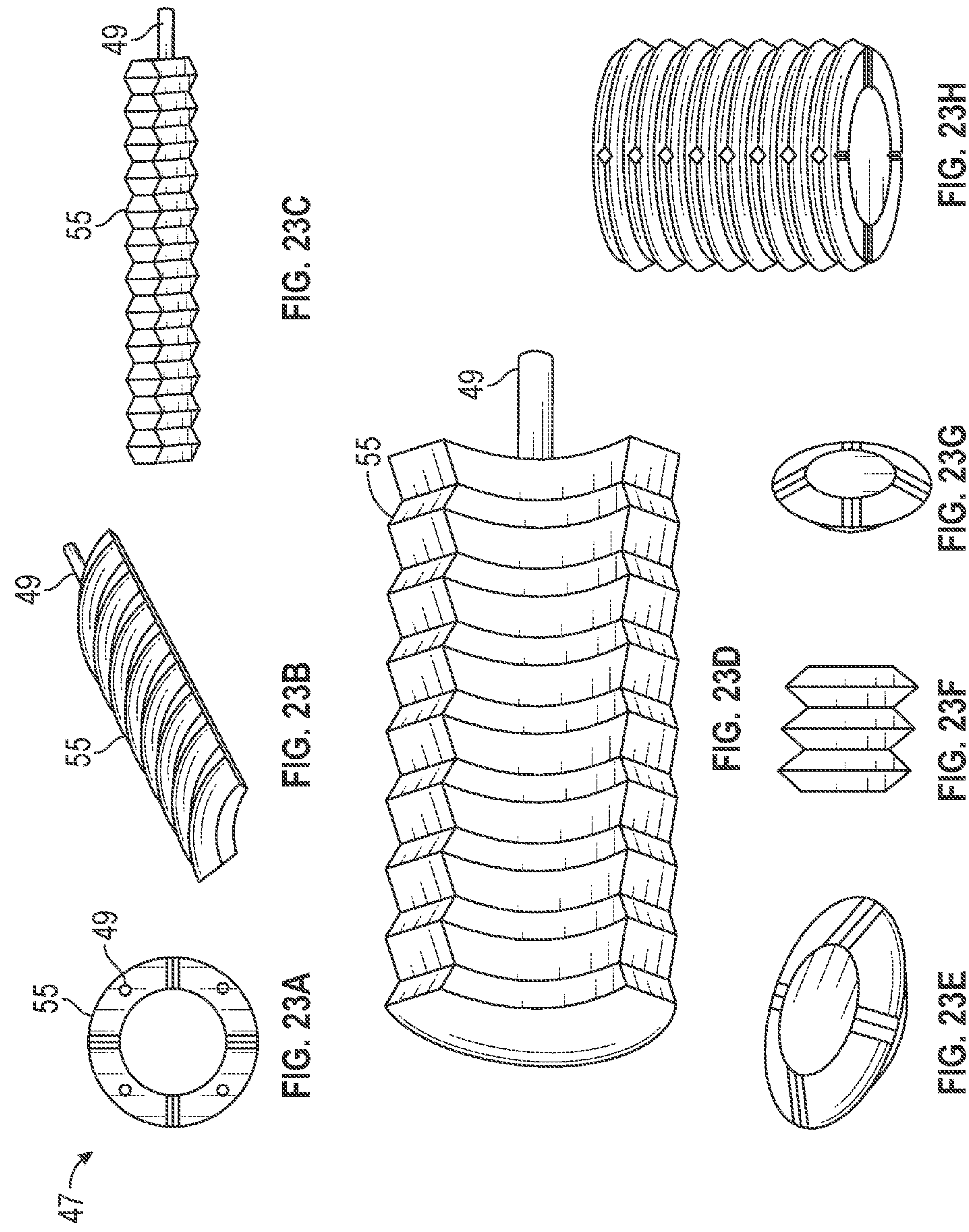
FIGS. 23A-23H show exemplary quarter bellows designs.

The bellows may comprise a plurality of unit bellows. For example, two, three, four or more unit bellows may be separately manufactured and then assembled to form a full circle of bellows, essentially as shown in FIGS. 20A-20F. For example, quarter bellows 55 having a medium channel 49 may be assembled with other quarter bellows to form bellows 47 shown in FIG. 23A (cross sectional view). Bellows 47 may have an outer diameter of about 1 inch and/or an inner diameter of about ⅝ inch. Quarter bellows 55 may be separately manufactured, as shown in FIG. 23B (prosective view showing the outer layer), FIG. 23C (side view), FIG. 23D (prosective view showing the inner layer). Identical unit bellows may be assembled, and in certain embodiments, different unit bellows may be assembled to form a full bellows. For example, unit bellows of different lengths (otherwise identical) may be assembled. In other examples, two quarter bellows and one half bellow may be assembled to form a full bellows. The unit bellows may also be separately manufactured in various parts shown in FIG. 23E, FIG. 23F, and FIG. 23G, and the parts are then assembled to form a full bellows as shown in FIG. 23H. Note each of the unit bellows in FIG. 23H may have a separate medium channel 49 such that each unit bellows may be controlled independently from other unit bellows in the same assembly.

In some aspects, the unit bellows design provides the advantage of selectively and/or preferentially inflating and/or deflating the unit bellows. For example, a full bellows may be assembled from a plurality of unit bellows, and the unit bellows may be identical or different. When the unit bellows are different, for example, in the case of two quarter bellows and one half bellows forming a full bellows, the half bellows may be selectively and/or preferentially inflated to articuate the distal portion of the inner tube to one direction. If adjustment of the bending direction is needed, one of the two quarter bellows may be selectively and/or preferentially inflated to fine tune the articuation the distal portion of the inner tube. When the unit bellows are identical, fine tuning the articuation is also possible. In the case of four quarter bellows forming a full bellows, one, two, or three of the quarter bellows may be inflated, while the remaining quarter bellows is/are deflated, not inflated, or inflated to a greater or lesser degree. Alternatively, one, two, or three of the quarter bellows may be deflated, while the remaining quarter bellows is/are inflated, not deflated, or deflated to a greater or lesser degree. A suitable combination of the inflation/deflation statuses of the unit bellows may be used to effect controllable and/or precise articulation of the inner member and/or the outer member, such as a distal portion of the inner member (e.g., the inner tube), thereby allowing the device to follow the curves of the body cavity during the movement. In some aspects, the controllable articulation and the ability to fine tune the articulation avoids or reduces stretching of the body cavity wall, thereby avoiding or reducing discomfort during the procedure.

In some embodiments, the multiple balloon/bellows/channel design (e.g., as shown in FIGS. 17A-17D) and/or the unit bellows design (e.g., as shown in FIGS. 23A-23H) may be used to allow and/or control the rotation or articulation of a distal tip of the device disclosed herein, e.g., the distal portion of the inner tube. In some embodiments, the distal portion of the inner tube can form an angle from 0 degree to 180 degree relative to a body portion of the device such as a body portion of the inner tube. For example, the angle between the distal portion of the inner tube and the body portion of the device can be about 30 degrees, about 45 degrees, about 60 degrees, about 75 degrees, about 90 degrees, about 105 degrees, about 120 degrees, about 135 degrees, about 150 degrees, about 165 degrees, or about 180 degrees.

Figure 24:
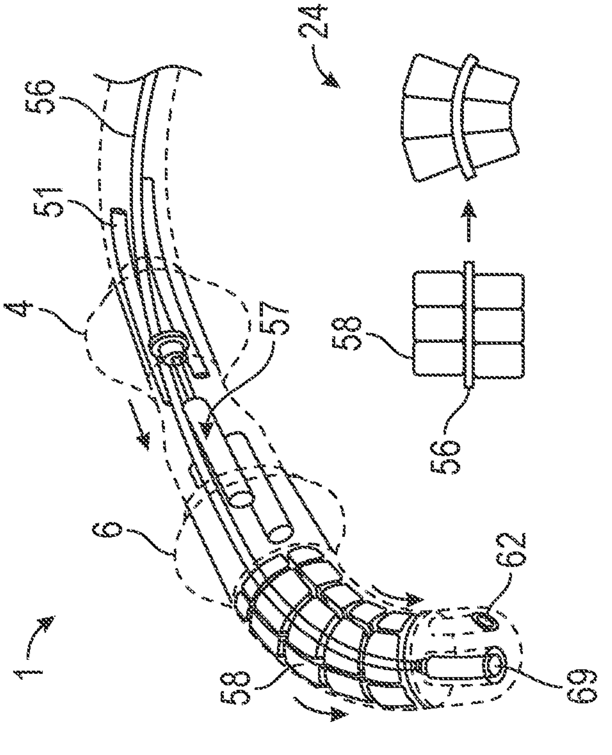
FIG. 24 shows an exemplary device comprising a propulsion mechanism (e.g., hydraulic propulsion) and an articulation mechanism.

In any of the preceding embodiments, the device may comprises a soft robot articulation mechanism and/or a hydraulic propulsion or driving mechanism. For example, as shown in FIG. 24, the device 1 comprises one or more hydraulic actuator 57 in between the first controllably expandable element 4 and the second controllably expandable element 6. Engagement of the inner member and outer member to the hydraulic actuator effects the sliding movement between the outer member and the inner member of the device. The device further comprises a plurality of soft, compliant fluid channels 51 running longitudinally through the device, and individual inflation and deflation of said channels with liquid or air effects the bending of the tip of the device. The device may also have a backbone 56 that flexes but does not change length, and the soft robot structures 58 allow flexing of the backbone to effect articulation of the device. As such, the distal portion of the device (such as the distal portion of the inner member) may be controlled and/or fine tuned.

In any of the preceding embodiments, the device may comprises a hydraulic articulation and/or propulsion mechanism. For example, the device 1 comprises one or more hydraulic actuator 57 in between the first controllably expandable element 4 and the second controllably expandable element 6. Engagement of the inner member and outer member to the hydraulic actuator effects the sliding movement between the outer member and the inner member of the device. The device further comprises a plurality of soft, compliant fluid channels 59 running longitudinally through the device, and individual inflation and deflation of said channels with liquid or air effects the bending of the tip of the device. The device may also have a backbone 56 that flexes but does not change length, and the soft robot structures 58 allow flexing of the backbone to effect articulation of the device. As such, the distal portion of the device (such as the distal portion of the inner member) may be controlled and/or fine tuned.

Figure 25A:
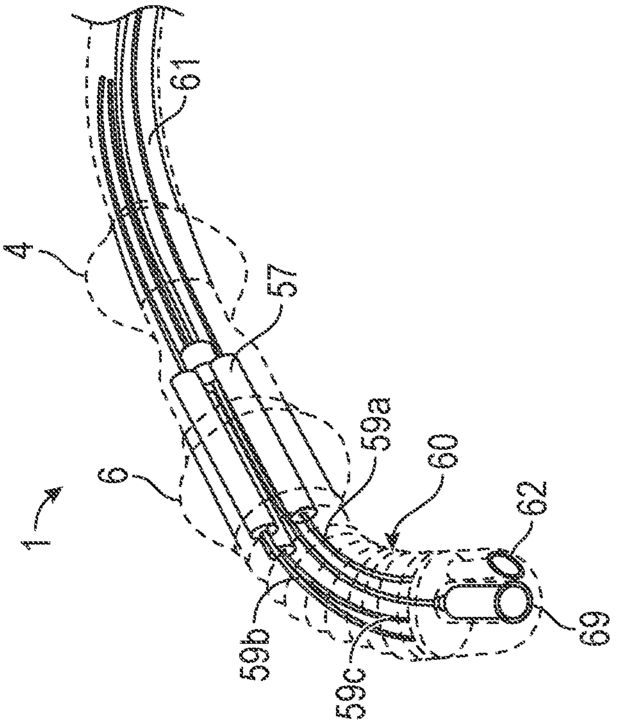
FIGS. 25A-25C show exemplary devices comprising a hydraulic articulation and/or propulsion mechanism.
Figure 25B:
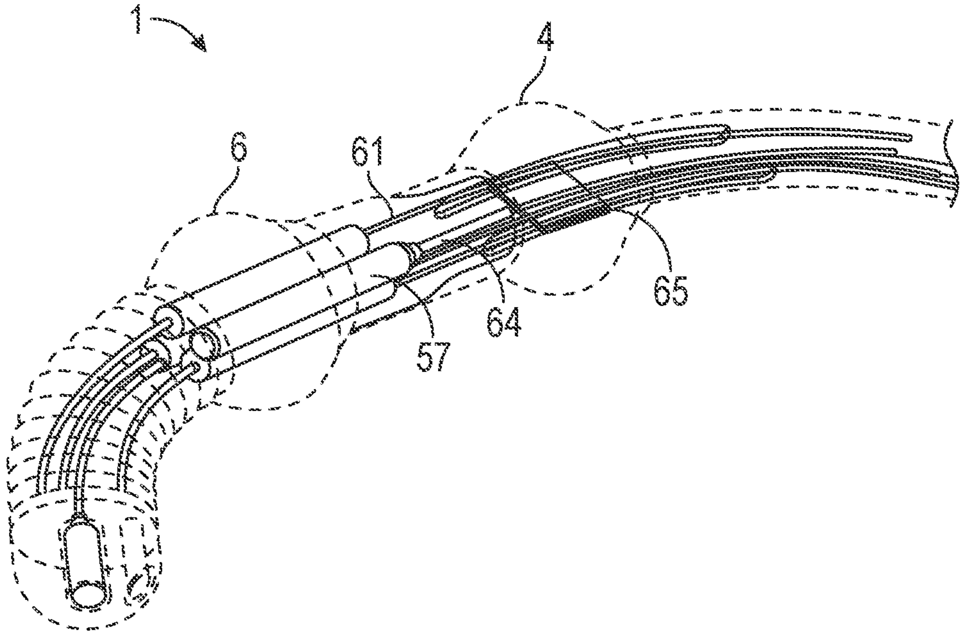
Figure 25C:
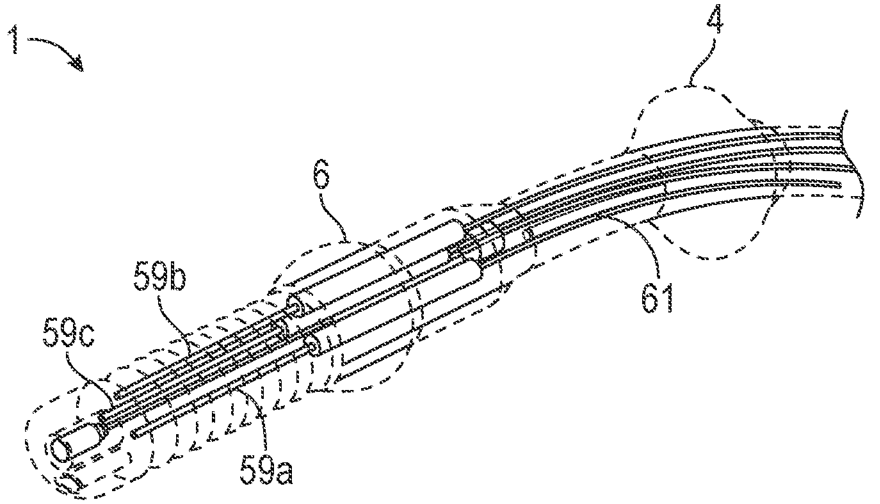

In any of the preceding embodiments, the device may comprises a hydraulic articulation and propulsion mechanism. For example, as shown in FIG. 25A, the device 1 comprises one or more hydraulic actuator 57 (connected to power via one or more hydraulic lines 61) in between the first controllably expandable element 4 and the second controllably expandable element 6. The device may be driven by an articulation movement powered by hydraulic actuated flexible cylinders and/or rods 59*a*, 59*b*, and 59*c* to bend the tip of the device. For example, the three hydraulically powered flex rods may enable the instrument to bend when individually extended/retracted with non-compressible fluid. As shown in the figure, flex rod 59*a* may contract, thereby pulling the tip of the device to the left. Alternatively, or at the same time, flex rod 59*b* and/or 59*c* may extend, thereby pushing the tip of the device to the left. The tip of the device may comprise working channel opening 62 and/or camera 63. During the movement, flex frame 60 allows for tight bend radius. FIG. 25B shows the one or more hydraulic actuator 57 (connected to power via one or more hydraulic lines 61) may comprise a soft cylinder. In addition, it may be connected to a flex rod 64 which is in turn connected an adjustable balloon assembly 65. Thus, flex rod 64 may contract, thereby pulling the first controllably expandable element 4 toward the tip of the device and closer to the second controllably expandable element 6. FIG. 25C shows the one or more hydraulic actuator 57 (connected to power via one or more hydraulic lines 61) may comprise a hydraulic piston. Flex rods 59*a*, 59*b*, and 59*c* are connected to the hydraulic piston, which may pull and/or push the first controllably expandable element 4 and/or the second controllably expandable element 6.

Figure 26A:
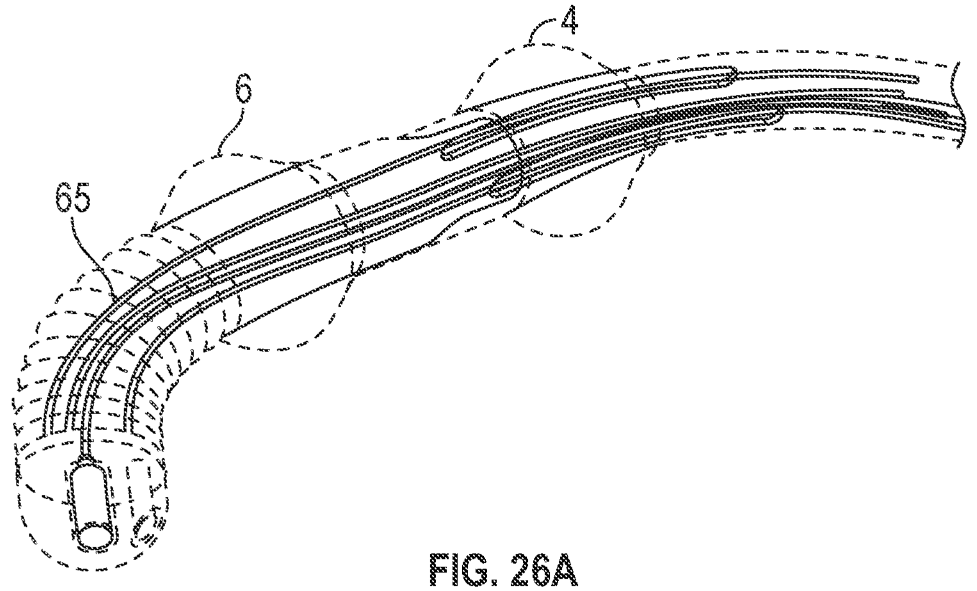
FIG. 26A shows an exemplary device comprising a cable articulation and/or propulsion mechanism.
Figure 26B:
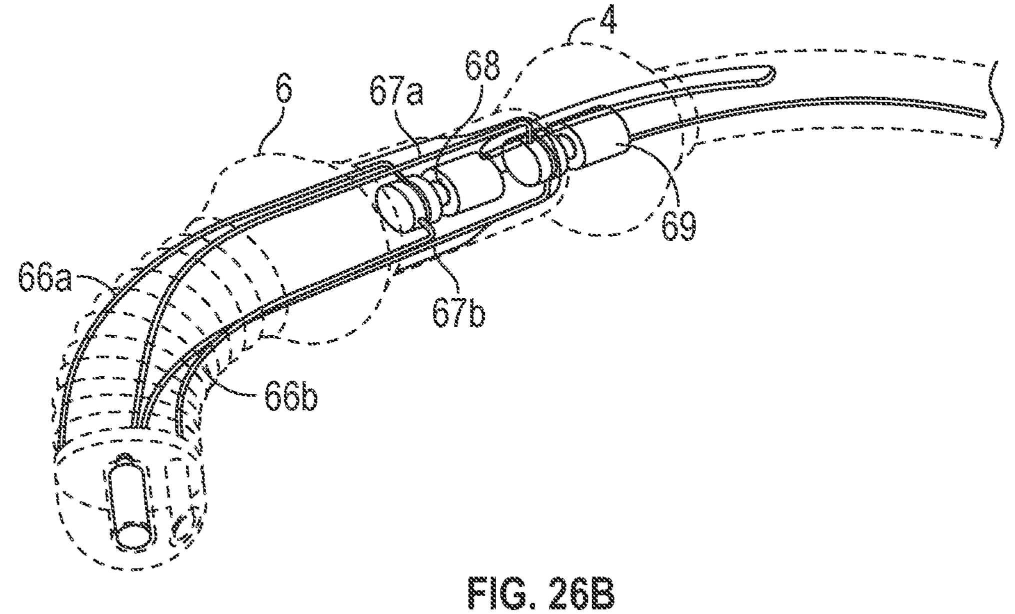
FIG. 26B shows an exemplary device comprising a motor/pulley articulation mechanism.
Figure 26C:
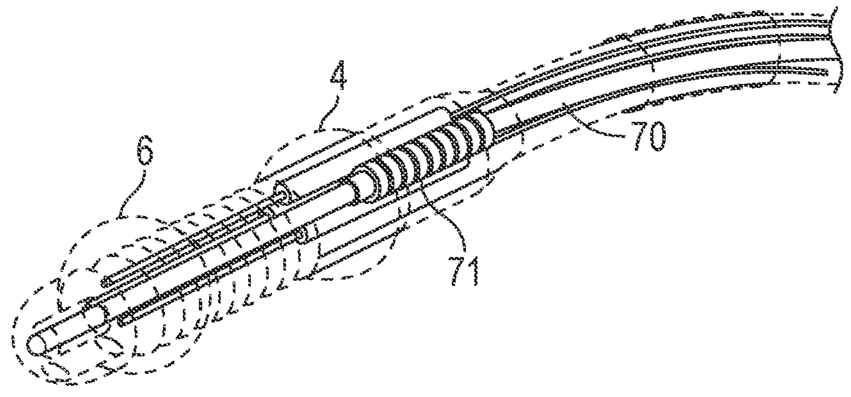
FIG. 26C shows an exemplary device comprising a linear servo motor propulsion mechanism.

In any of the preceding embodiments, the device may comprises one or more of the following mechanisms: a cable articulation and/or propulsion mechanism, a motor/pulley articulation mechanism, and a linear servo motor propulsion mechanism. For example, as shown in FIG. 26A, a plurality of cables 65 are connected to an actuator to control the sliding movement between the outer member and the inner member of the device, and/or to control the articulation of the tip of the device. The device may comprise cables 65 running longitudinally through the device, the distal ends of said cables fixed in the tip of the device. The cables may be coupled with a plurality of motor-pulley systems, and individual pulling and pushing of said cables by the motor-pulley systems effects the bending of the tip of the device. As shown in FIG. 26B, the device may comprise a plurality of closed loop cables 66*a*/66*b* and 67*a*/67*b* running longitudinally through the device, the distal ends of said cables fixed in the tip of the device. The cables are coupled with a plurality of motor-pulley systems 68 and 69, respectively, and individual pulling and pushing of said cables by the motor-pulley systems effects the bending of the tip of the device. For example, closed loop cables 66*a*/66*b* are connected to motor-pulley system 68 on one end and the tip of the device on the other end, forming a closed loop. Similarly, closed loop cables 67*a*/67*b* are connected to motor-pulley system 69 on one end and the tip of the device on the other end, forming another closed loop. A flexible housing unit may surround the cable assembly to contain the articulation mechanism. The device may comprises a three phase servo motor actuator comprising a guidewire 70. As shown in FIG. 26C, linearly oriented coils 71 are energized in sequence to propel the balloon mechanism (e.g., a balloon anchor), such as balloons 4 and/or 6, forward and backward. The coils may be configured to slidably move along the guidewire. The device further comprises a bidirectional magnet installed on the balloon mechanism in order to integrate with the magnetic linear actuator.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms “a,” “an,” and “the” include plural referents unless the context clearly dictates otherwise. For example, “a” or “an” means “at least one” or “one or more.” It is understood that aspects and variations described herein include “consisting” and/or “consisting essentially of” aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term “about” as used herein refers to the usual error range for the respective value readily known. Reference to “about” a value or parameter herein includes (and describes) embodiments that are directed to that value or parameter per se. For example, description referring to “about X” includes description of “X”.

As used herein, a “subject” is a mammal, such as a human or other animal, and typically is human.

Exemplary Embodiments

Among the provided embodiments are:

Embodiment 1. A device configured to move within a body cavity, said device comprising: an outer member comprising a distal end, a proximal end, and a lumen between the distal end and the proximal end; an inner member slidably disposed in the lumen of the outer member, wherein the inner member comprises a distal end and a proximal end; a first controllably expandable element disposed on the outer member; a second controllably expandable element disposed on the outer member or on the inner member; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

Embodiment 2. A device configured to move within a body cavity, said device comprising: an outer member comprising a distal end, a proximal end, a lumen between the distal end and the proximal end, and a first controllably expandable element; an inner member slidably disposed in the lumen of the outer member, wherein the inner member comprises a distal end, a proximal end, and a second controllably expandable element; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

Embodiment 3. A device configured to move within a body cavity, said device comprising: an outer member comprising a distal end, a proximal end, a lumen between the distal end and the proximal end, a first controllably expandable element, and a second controllably expandable element; an inner member slidably disposed in the lumen of the outer member, wherein the inner member comprises a distal end and a proximal end; a connector that connects the outer member and the inner member; and an actuating member capable of effecting sliding movement between the outer member and the inner member, thereby alternating extensions and retractions of a distance between the first and second controllably expandable elements, wherein the first and second controllably expandable elements are capable of expanding radially outwardly to engage a wall of a body cavity.

Embodiment 4. The device of any one of Embodiments 1-3, wherein the inner member comprises one or more aperture on the distal end.

Embodiment 5. The device of any one of Embodiments 1-4, wherein the inner member comprises one or more channel.

Embodiment 6. The device of any one of Embodiments 1-5, further comprising an articulation element capable of effecting articulation of the distal end of the inner member or the distal end of the outer member.

Embodiment 7. The device of Embodiment 6, wherein the articulation element is capable of effecting articulation of the distal end of the inner member.

Embodiment 8. The device of any one of Embodiments 1-7, wherein the first controllably expandable element is disposed on an outer surface of the outer member.

Embodiment 9. The device of any one of Embodiments 1-8, wherein the second controllably expandable element is disposed on an outer surface of the inner member.

Embodiment 10. The device of any one of Embodiments 1-7, wherein the first and second controllably expandable elements are both disposed on the outer member.

Embodiment 11. The device of any one of Embodiments 1-10, wherein the inner member extends through the first lumen of the outer member.

Embodiment 12. The device of any one of Embodiments 1-11, wherein the second controllably expandable element is outside the first lumen of the outer member.

Embodiment 13. The device of any one of Embodiments 1-12, wherein the first controllably expandable element is a first balloon.

Embodiment 14. The device of any one of Embodiments 1-13, wherein the second controllably expandable element is a second balloon.

Embodiment 15. The device of any one of Embodiments 1-14, further comprising a first medium channel connected to the first controllably expandable element, wherein the medium comprises a gas, a liquid, or a mixture thereof (e.g., a vapor).

Embodiment 16. The device of Embodiment 15, wherein the first medium channel is inside the outer member, outside the outer member, or partially inside and partially outside the outer member.

Embodiment 17. The device of any one of Embodiments 1-16, further comprising a second medium channel connected to the second controllably expandable element, wherein the medium comprises a gas, a liquid, or a mixture thereof (e.g., a vapor).

Embodiment 18. The device of Embodiment 17, wherein the second medium channel is inside the inner member, outside the inner member, or partially inside and partially outside the inner member.

Embodiment 19. The device of Embodiment 17 or 18, wherein the first and second medium channels are separate channels.

Embodiment 20. The device of any one of Embodiments 1-19, further comprising a control member.

Embodiment 21. The device of Embodiment 20, wherein the control member is configured to independently expand and/or contract the first and second controllably expandable elements.

Embodiment 22. The device of Embodiment 20 or 21, wherein the control member is configured to control the actuating member, thereby controlling the sliding movement between the outer member and the inner member.

Embodiment 23. The device of any one of Embodiments 1-22, wherein the inner member comprises a body portion and a distal portion comprising the distal end of the inner member.

Embodiment 24. The device of Embodiment 23, wherein the second controllably expandable element is disposed on the distal portion of the inner member.

Embodiment 25. The device of Embodiment 23 or 24, wherein the distal end of the inner member comprises two or more apertures.

Embodiment 26. The device of Embodiment 25, wherein at least one of the apertures is for an image capturing device.

Embodiment 27. The device of Embodiment 25 or 26, wherein at least one of the apertures is for a gas, liquid, or suction channel.

Embodiment 28. The device of any one of Embodiments 23-27, wherein the proximal end of the distal portion comprises one or more controllably expandable base.

Embodiment 29. The device of any one of Embodiments 23-28, comprising an articulation element capable of effecting articulation of the distal end of the inner member.

Embodiment 30. The device of Embodiment 29, wherein the articulation element comprises a motor.

Embodiment 31. The device of Embodiment 29 or 30, wherein the articulation element comprises one or more controllably expandable base on the proximal end of the distal portion.

Embodiment 32. The device of Embodiment 31, wherein the one or more controllably expandable base is configured to inflate and/or deflate, thereby effecting articulation of the distal portion in a direction transverse to the longitudinal axis of the body portion.

Embodiment 33. The device of Embodiment 31 or 32, further comprising a medium channel connected to the one or more controllably expandable base, wherein the medium comprises a gas, a liquid, or a mixture thereof (e.g., a vapor).

Embodiment 34. The device of any one of Embodiments 23-33, wherein the body portion of the inner member comprises walls defining an inner cavity and a nut inside the inner cavity, wherein the nut is securely fixed to the walls via one or more inner member arm.

Embodiment 35. The device of Embodiment 34, wherein the body portion of the inner member further comprises one or more longitudinal slit.

Embodiment 36. The device of Embodiment 35, wherein the outer member comprises one or more outer member arm through the one or more longitudinal slit of the inner member, wherein the one or more outer member arm is connected to a screw engaging the nut, thereby connecting the outer member and the inner member.

Embodiment 37. The device of Embodiment 36, wherein the screw is connected to a motor capable of effecting relative rotation of the screw and the nut, thereby effecting the sliding movement between the outer member and the inner member.

Embodiment 38. The device of any one of Embodiments 35-37, wherein the one or more longitudinal slit is configured to prevent the inner member and the outer member from becoming disconnected during the sliding movement.

Embodiment 39. The device of any one of Embodiments 1-33, comprising a controllably expandable structure configured to expand or contract longitudinally, thereby effecting the sliding movement between the outer member and the inner member.

Embodiment 40. The device of Embodiment 39, wherein the controllably expandable structure is distal to the first controllably expandable element, wherein longitudinal expansion and/or contraction of the controllably expandable structure effects a longitudinal movement of the first controllably expandable element relative to the second controllably expandable element.

Embodiment 41. The device of Embodiment 39, wherein the controllably expandable structure is proximal to the first controllably expandable element, wherein longitudinal expansion and/or contraction of the controllably expandable structure effects a longitudinal movement of the first controllably expandable element relative to the second controllably expandable element.

Embodiment 42. The device of Embodiment 39, comprising two controllably expandable structures, one of which is distal to the first controllably expandable element while the other one is proximal to the first controllably expandable element, wherein coordinated longitudinal expansion and/or contraction of the two controllably expandable structures effects a longitudinal movement of the first controllably expandable element relative to the second controllably expandable element.

Embodiment 43. The device of Embodiment 39, wherein the controllably expandable structure is distal to the second controllably expandable element, wherein longitudinal expansion and/or contraction of the controllably expandable structure effects a longitudinal movement of the first controllably expandable element relative to the second controllably expandable element.

Embodiment 44. The device of Embodiment 39, wherein the controllably expandable structure is proximal to the second controllably expandable element, wherein longitudinal expansion and/or contraction of the controllably expandable structure effects a longitudinal movement of the first controllably expandable element relative to the second controllably expandable element.

Embodiment 45. The device of Embodiment 39, comprising two controllably expandable structures, one of which is distal to the second controllably expandable element while the other one is proximal to the second controllably expandable element, wherein coordinated longitudinal expansion and/or contraction of the two controllably expandable structures effects a longitudinal movement of the first controllably expandable element relative to the second controllably expandable element.

Embodiment 46. The device of Embodiment 39, wherein the controllably expandable structure is between the first controllably expandable element and the second controllably expandable element, wherein longitudinal expansion and/or contraction of the controllably expandable structure effects a longitudinal movement of the first controllably expandable element relative to the second controllably expandable element.

Embodiment 47. The device of any one of Embodiments 39-46, wherein the controllably expandable structure comprises a telescoping balloon.

Embodiment 48. The device of any one of Embodiments 39-47, wherein the controllably expandable structure comprises a shape-memory alloy.

Embodiment 49. The device of any one of Embodiments 39-48, wherein the controllably expandable structure comprises a compliant balloon and/or a semi-compliant balloon.

Embodiment 50. The device of any one of Embodiments 39-49, wherein the controllably expandable structure comprises a bellows, e.g., a compliant bellows.

Embodiment 51. The device of any one of Embodiments 1-33, comprising a plurality of controllably expandable structures between the first controllably expandable element and the second controllably expandable element, wherein expansion and/or contraction of the plurality of controllably expandable structures effects a longitudinal movement of the first controllably expandable element relative to the second controllably expandable element.

Embodiment 52. The device of Embodiment 51, wherein the plurality of controllably expandable structures form a helix.

Embodiment 53. The device of Embodiment 51 or 52, wherein expansion and/or contraction of the plurality of controllably expandable structures effects a rotational movement of the first or second controllably expandable element relative to each other.

Embodiment 54. The device of Embodiment 53, wherein the first or second controllably expandable element is in a contracted or deflated state during the rotational movement.

Embodiment 55. The device of any of Embodiments 51-54, comprising three or more controllably expandable structures.

Embodiment 56. The device of any of Embodiments 51-55, wherein expansion and/or contraction of the plurality of controllably expandable structures effects articulation of a distal portion of the inner and/or outer member in a direction transverse to the longitudinal axis of a body portion of the inner and/or outer member.

Embodiment 57. The device of any one of Embodiments 51-56, wherein the controllably expandable structures comprise one or more compliant balloon and/or one or more semi-compliant balloon.

Embodiment 58. The device of any one of Embodiments 51-57, wherein the controllably expandable structures comprise one or more bellows, e.g., a compliant bellows.

Embodiment 59. The device of Embodiment 51, wherein the plurality of controllably expandable structures comprise two or more pressure balloons.

Embodiment 60. The device of Embodiment 51, wherein the plurality of controllably expandable structures comprise a pressure balloon, a pressure chamber, or combinations thereof.

Embodiment 61. The device of Embodiment 60, wherein the plurality of controllably expandable structures comprise three or four pressure balloons.

Embodiment 62. The device of Embodiment 60, wherein the plurality of controllably expandable structures comprise three or four pressure chambers.

Embodiment 63. The device of any one of Embodiments 60-62, wherein a subset of the plurality of controllably expandable structures are configured to selectively inflate and/or deflate, thereby effecting articulation of the second controllably expandable element in a direction transverse to the longitudinal axis of the outer member.

Embodiment 64. The device of any one of Embodiments 1-63, further comprising a plurality of controllably expandable structures distal to the second controllably expandable element, wherein a subset of the plurality of controllably expandable structures are configured to selectively inflate and/or deflate, thereby effecting articulation of the distal end of the inner member in a direction transverse to the longitudinal axis of the outer member.

Embodiment 65. The device of any one of Embodiments 1-64, wherein the first controllably expandable element comprises a plurality of treads on a surface configured to engage the wall of the body cavity.

Embodiment 66. The device of any one of Embodiments 1-65, wherein the second controllably expandable element comprises a plurality of treads on a surface configured to engage the wall of the body cavity.

Embodiment 67. A method for locomotion of the device of any one of Embodiments 1-66 through a body cavity, the method comprising: (i) expanding the second controllably expandable element radially outwardly to engage a wall of the body cavity, optionally while the first controllably expandable elements is not radially outwardly expanded, thereby fixing the second controllably expandable element to a first position in the body cavity; (ii) effecting sliding movement between the outer member and the inner member to retract the distance between the first and second controllably expandable elements; (iii) expanding the first controllably expandable element radially outwardly to engage a wall of the body cavity; (iv) contracting the second controllably expandable elements radially and inwardly; (v) effecting sliding movement between the outer member and the inner member to extend the distance between the first and second controllably expandable elements; and (vi) expanding the second controllably expandable element radially outwardly to engage a wall of the body cavity, optionally while the first controllably expandable elements is not radially outwardly expanded, thereby fixing the second controllably expandable element to a second position in the body cavity.

Embodiment 68. The method of Embodiment 67, comprising repeating steps of (ii)-(vi).

Embodiment 69. A method for locomotion of the device of any one of embodiments 1-66 through a body cavity, the method comprising: (i) expanding the first controllably expandable element radially outwardly to engage a wall of the body cavity, optionally while the second controllably expandable elements is not radially outwardly expanded, thereby fixing the first controllably expandable element to a first position in the body cavity; (ii) while the second controllably expandable elements is not radially outwardly expanded, effecting sliding movement between the outer member and the inner member to extend the distance between the first and second controllably expandable elements; (iii) expanding the second controllably expandable element radially outwardly to engage a wall of the body cavity; (iv) contracting the first controllably expandable elements radially and inwardly; (v) effecting sliding movement between the outer member and the inner member to retract the distance between the first and second controllably expandable elements; and (vi) expanding the first controllably expandable element radially outwardly to engage a wall of the body cavity, optionally while the second controllably expandable elements is not radially outwardly expanded, thereby fixing the first controllably expandable element to a second position in the body cavity.

Embodiment 70. The method of Embodiment 69, comprising repeating steps of (ii)-(vi).

Embodiment 71. The method of any one of Embodiments 67-70, further comprising delivering a substance into the body cavity through one or more channel of the inner member.

Embodiment 72. The method of any one of Embodiments 67-71, further comprising removing a substance from the body cavity through one or more channel of the inner member.

Embodiment 73. The method of any one of Embodiments 67-72, further comprising capturing an image of the body cavity through one or more channel of the inner member.

Embodiment 74. The method of any one of Embodiments 67-73, further comprising performing an operation of a tissue within the body cavity through one or more channel of the inner member.

Embodiment 75. The device or method of any one of Embodiments 1-74, wherein the body cavity is a vascular body lumen, a digestive body lumen, a respiratory body lumen, or a urinary body lumen.

Embodiment 76. The device of Embodiment 75, wherein the digestive body lumen is a gastrointestinal tract.

Embodiment 77. The device of Embodiment 76, wherein the gastrointestinal tract is small intestine.

Embodiment 78. The device of Embodiment 76, wherein the gastrointestinal tract is duodenum, jejunum, or ileum.

Embodiment 79. The device of Embodiment 76, wherein the gastrointestinal tract is colon.

Embodiment 80. The device of Embodiment 76, wherein the gastrointestinal tract is esophagus.

Embodiment 81. The device of Embodiment 76, wherein the gastrointestinal tract is stomach.

The invention claimed is:

1. A self-driving device configured to move within a gastrointestinal tract, said device comprising:

an outer member comprising a distal end, a proximal end, and a lumen between the distal end and the proximal end;

an inner member slidably disposed in the lumen of the outer member, wherein the inner member comprises a distal end and a proximal end;

a first controllably expandable element disposed on the outer member;

a second controllably expandable element disposed on the inner member;

a connector that connects the outer member and the inner member; and an actuating member capable of effecting sliding movement between the outer member and the inner member, thereby alternating extensions and retractions of a distance between the first and second controllably expandable elements to move the device within the gastrointestinal tract, wherein:

(i) the first controllably expandable element is capable of expanding radially outwardly to engage a wall of the gastrointestinal tract while the second controllably expandable element is not radially outwardly expanded; and (ii) the second controllably expandable element is capable of expanding radially outwardly to engage a wall of the gastrointestinal tract while the first controllably expandable element is not radially outwardly expanded; and an articulation element capable of effecting articulation of the distal end of the inner member or the distal end of the outer member, wherein the articulation element comprises a motor-pulley articulation system and cables coupled thereto, wherein the cables comprise distal ends fixed in the distal end of the inner member or the distal end of the outer member, and the motor-pulley articulation system is configured to pull and push the cables to effect bending of the distal end of the inner member or the distal end of the outer member.

2. The device of claim 1, wherein the first controllably expandable element is disposed on the outer member and the second controllably expandable element is disposed on the inner member.

3. The device of claim 1, wherein the inner member comprises one or more aperture on the distal end and/or one or more channel.

4. The device of claim 1, wherein i) the first controllably expandable element is disposed on an outer surface of the outer member, and wherein the second controllably expandable element is disposed on an outer surface of the inner member; or ii) the first and second controllably expandable elements are both disposed on the outer member.

5. The device of claim 1, wherein the inner member extends through the first lumen of the outer member, wherein the second controllably expandable element is outside the first lumen of the outer member, wherein the first controllably expandable element is a first balloon, and wherein the second controllably expandable element is a second balloon.

6. The device of claim 1, further comprising a first medium channel connected to the first controllably expandable element and a second medium channel connected to the second controllably expandable element, wherein the first medium channel and the second medium channel are inside the outer member, outside the outer member, or partially inside and partially outside the outer member, wherein the medium comprises a gas, a liquid, or a mixture thereof, and wherein the first and second medium channels are separate channels.

7. The device of claim 1, wherein the inner member comprises a body portion and a distal portion comprising the distal end of the inner member, wherein the second controllably expandable element is disposed on the distal portion of the inner member.

8. The device of claim 7, wherein the body portion of the inner member comprises walls defining an inner cavity and a nut inside the inner cavity, wherein the nut is securely fixed to the walls via one or more inner member arm.

9. The device of claim 8, wherein the body portion of the inner member further comprises one or more longitudinal slit, wherein the outer member comprises one or more outer member arm through the one or more longitudinal slit of the inner member; wherein the one or more outer member arm is connected to a screw engaging the nut, thereby connecting the outer member and the inner member; wherein the screw is connected to a motor capable of effecting relative rotation of the screw and the nut, thereby effecting the sliding movement between the outer member and the inner member; and wherein the one or more longitudinal slit is configured to prevent the inner member and the outer member from becoming disconnected during the sliding movement.

10. The device of claim 7, wherein the distal end of the inner member comprises two or more apertures, wherein at least one of the apertures is for an image capturing device, and/or at least one of the apertures is for a gas, liquid, or suction channel.

11. The device of claim 1, comprising a controllably expandable structure configured to expand or contract longitudinally, thereby effecting the sliding movement between the outer member and the inner member, wherein the controllably expandable structure comprises a telescoping balloon, a shape-memory alloy, a compliant balloon, a semi-compliant balloon, a bellows or any combination thereof, and wherein:

i) the controllably expandable structure is distal to the first controllably expandable element, wherein longitudinal expansion and/or contraction of the controllably expandable structure effects a longitudinal movement of the first controllably expandable element relative to the second controllably expandable element;

ii) the controllably expandable structure is distal to the first controllably expandable element, wherein longitudinal expansion and/or contraction of the controllably expandable structure effects a longitudinal movement of the first controllably expandable element relative to the second controllably expandable element;

iii) the controllably expandable structure is distal to the second controllably expandable element, wherein longitudinal expansion and/or contraction of the controllably expandable structure effects a longitudinal movement of the first controllably expandable element relative to the second controllably expandable element;

iv) the controllably expandable structure is proximal to the second controllably expandable element, wherein longitudinal expansion and/or contraction of the controllably expandable structure effects a longitudinal movement of the first controllably expandable element relative to the second controllably expandable element; or v) the controllably expandable structure is between the first controllably expandable element and the second controllably expandable element, wherein longitudinal expansion and/or contraction of the controllably expandable structure effects a longitudinal movement of the first controllably expandable element relative to the second controllably expandable element.

12. The device of claim 11, comprising two controllably expandable structures, wherein:

(i) one of which is distal to the first controllably expandable element while the other one is proximal to the first controllably expandable element, wherein coordinated longitudinal expansion and/or contraction of the two controllably expandable structures effects a longitudinal movement of the first controllably expandable element relative to the second controllably expandable element; or (ii) one of which is distal to the second controllably expandable element while the other one is proximal to the second controllably expandable element, wherein coordinated longitudinal expansion and/or contraction of the two controllably expandable structures effects a longitudinal movement of the first controllably expandable element relative to the second controllably expandable element.

13. The device of claim 1, comprising a plurality of controllably expandable structures between the first controllably expandable element and the second controllably expandable element, wherein expansion and/or contraction of the plurality of controllably expandable structures effects a longitudinal movement of the first controllably expandable element relative to the second controllably expandable element.

14. The device of claim 13, wherein the controllably expandable structures comprise one or more compliant balloon and/or one or more semi-compliant balloon, wherein:

i) the controllably expandable structures comprise one or more bellows;

ii) the plurality of controllably expandable structures comprise two or more pressure balloons, a pressure balloon, a pressure chamber, three or four pressure balloons, or three or four pressure chambers, or combinations thereof; or iii) a subset of the plurality of controllably expandable structures are configured to selectively inflate and/or deflate, thereby effecting articulation of the second controllably expandable element in a direction transverse to the longitudinal axis of the outer member.

15. The device of claim 13, wherein expansion and/or contraction of the plurality of controllably expandable structures effects:

(i) a rotational movement of the first or second controllably expandable element relative to each other; or (ii) articulation of a distal portion of the inner and/or outer member in a direction transverse to the longitudinal axis of a body portion of the inner and/or outer member.

16. The device of claim 1, wherein:

the first controllably expandable element comprises a plurality of treads on a surface configured to engage the wall of the gastrointestinal tract, or the second controllably expandable element comprises a plurality of treads on a surface configured to engage the wall of the gastrointestinal tract.

17. The device of claim 16, wherein the device further comprises a plurality of controllably expandable structures distal to the second controllably expandable element, wherein a subset of the plurality of controllably expandable structures are configured to selectively inflate and/or deflate, thereby effecting articulation of the distal end of the inner member in a direction transverse to the longitudinal axis of the outer member.

18. A method for locomotion of the self-driving device of claim 1 through the gastrointestinal tract, the method comprising:

i) expanding the second controllably expandable element radially outwardly to engage a wall of the gastrointestinal tract, thereby fixing the second controllably expandable element to a first position in the gastrointestinal tract;

ii) while the first controllably expandable elements is not radially outwardly expanded to engage a wall of the gastrointestinal tract, effecting sliding movement between the outer member and the inner member to retract the distance between the first and second controllably expandable elements;

iii) expanding the first controllably expandable element radially outwardly to engage a wall of the gastrointestinal tract;

iv) contracting the second controllably expandable elements radially and inwardly;

v) effecting sliding movement between the outer member and the inner member to extend the distance between the first and second controllably expandable elements; and vi) expanding the second controllably expandable element radially outwardly to engage a wall of the gastrointestinal tract, while the first controllably expandable elements is not radially outwardly expanded, thereby fixing the second controllably expandable element to a second position in the gastrointestinal tract.

19. The method of claim 18, comprising repeating steps of ii-vi.

20. The method of claim 18, further comprising i) delivering a substance into the gastrointestinal tract through one or more channel of the inner member;

ii) removing a substance from the gastrointestinal tract through one or more channel of the inner member;

iii) capturing an image of the gastrointestinal tract through one or more channel of the inner member; or iv) performing an operation of a tissue within the gastrointestinal tract through one or more channel of the inner member, or any combinations of i)-iv).

21. A method for locomotion of the self-driving device of claim 1 through a gastrointestinal tract, the method comprising:

i) expanding the first controllably expandable element radially outwardly to engage a wall of the gastrointestinal tract, thereby fixing the first controllably expandable element to a first position in the gastrointestinal tract;

ii) while the second controllably expandable elements is not radially outwardly expanded, effecting sliding movement between the outer member and the inner member to extend the distance between the first and second controllably expandable elements;

iii) expanding the second controllably expandable element radially outwardly to engage a wall of the gastrointestinal tract;

iv) contracting the first controllably expandable elements radially and inwardly;

v) effecting sliding movement between the outer member and the inner member to retract the distance between the first and second controllably expandable elements; and vi) expanding the first controllably expandable element radially outwardly to engage a wall of the gastrointestinal tract, while the second controllably expandable elements is not radially outwardly expanded, thereby fixing the first controllably expandable element to a second position in the gastrointestinal tract.

22. The method of claim 21, comprising repeating steps of ii-vi.

23. The device of claim 1, wherein the gastrointestinal tract is small intestine, duodenum, jejunum, ileum, colon, esophagus, or stomach.

* * * * *